United States Patent
Wang

(10) Patent No.: US 9,576,778 B2
(45) Date of Patent: Feb. 21, 2017

(54) DATA PROCESSING FOR MULTIPLEXED SPECTROMETRY

(71) Applicant: Agilent Technologies, Inc., Santa Clara, CA (US)

(72) Inventor: Jun Wang, San Jose, CA (US)

(73) Assignee: Agilent Technologies, Inc., Santa Clara, CA (US)

(*) Notice: Subject to any disclaimer, the term of this patent is extended or adjusted under 35 U.S.C. 154(b) by 0 days.

(21) Appl. No.: 14/686,569

(22) Filed: Apr. 14, 2015

(65) Prior Publication Data
US 2015/0364305 A1 Dec. 17, 2015

Related U.S. Application Data

(60) Provisional application No. 62/011,893, filed on Jun. 13, 2014.

(51) Int. Cl.
*H01J 49/00* (2006.01)
*H01J 49/40* (2006.01)
*G01N 27/62* (2006.01)

(52) U.S. Cl.
CPC ......... *H01J 49/0036* (2013.01); *G01N 27/622* (2013.01); *H01J 49/40* (2013.01)

(58) Field of Classification Search
USPC ....................................................... 250/282
See application file for complete search history.

(56) References Cited

U.S. PATENT DOCUMENTS

| | | | |
|---|---|---|---|
| 5,247,175 A * | 9/1993 | Schoen | H01J 49/0027 250/281 |
| 5,396,065 A | 3/1995 | Myerholtz et al. | |
| 5,644,503 A * | 7/1997 | Ito | G01N 30/8624 702/22 |
| 5,719,392 A | 2/1998 | Franzen | |
| 5,862,269 A * | 1/1999 | Cohen | G06T 5/20 382/275 |
| 6,300,626 B1 | 10/2001 | Brock et al. | |
| 7,075,064 B2 * | 7/2006 | Oliphant | G06K 9/00503 250/281 |
| 8,080,782 B2 | 12/2011 | Hidalgo et al. | |
| 8,324,565 B2 | 12/2012 | Mordehai et al. | |
| 2005/0001163 A1 | 1/2005 | Belov et al. | |

OTHER PUBLICATIONS

Ansgar Brock et al., "Hadamard Transform Time-of-Flight Mass Spectrometry", Anal. Chem. 1998, 70, 3735-3741.
Cherokee S. Hoaglund et al., "Three-Dimensional Ion Mobility/TOFMS Analysis of Electrosprayed Biomolecules", Anal. Chem. 1998, 70, 2236-2242.
Stormy L. Koeniger, et al., "Evidence for Many Resolvable Structures within Conformation Types of Electrosprayed Ubiquitin Ions", J. Phys. Chem. B 2006, 110, 7017-7021.

(Continued)

*Primary Examiner* — Phillip A Johnston

(57) ABSTRACT

Multiplexed spectrometry, such as multiplexed ion mobility spectrometry (IMS), time-of-flight mass spectrometry (TOFMS), or hybrid IM-TOFMS, is carried out on a sample, and the resulting measurement data are deconvoluted. Noise may be removed from the measurement data prior to deconvolution. Alternatively or additionally, noise may be removed from the deconvoluted data.

20 Claims, 9 Drawing Sheets

(56) References Cited

OTHER PUBLICATIONS

Richard N. Zare et al., "High-Speed Mass Spectrometry, Hadamard Transform Time-of-Flight Mass Spectrometry: More Signal, More of the Time", Angew. Chem. Int. Ed, 2003, 42, No. 1.
Joel R. Kimmel, et al, Effects of Modulation Defects on Hadamard Transform Time-of-flight Mass Spectrometry (HT-TOFMS); American Society for Mass Spectrometry, 2003, 1044-0305.

* cited by examiner

DATA PROCESSING FOR MULTIPLEXED SPECTROMETRY

RELATED APPLICATIONS

This application claims the benefit of U.S. Provisional Patent Application Ser. No. 62/011,893, filed Jun. 13, 2014, titled "DATA PROCESSING FOR MULTIPLEXED ION MOBILITY SPECTROMETRY AND TIME-OF-FLIGHT MASS SPECTROMETRY," the content of which is incorporated by reference herein in its entirety.

TECHNICAL FIELD

The present invention relates generally to spectrometry such as ion mobility spectrometry (IMS), time-of-flight mass spectrometry (TOFMS), and ion mobility-time-of-flight mass spectrometry (IM-TOFMS). The invention relates particularly to multiplexed techniques implemented in conjunction with spectrometry.

BACKGROUND

Ion mobility spectrometry (IMS) is a gas-phase ion separation technique in which ions become separated in time and space as they travel through a drift cell of known length containing a buffer gas of known composition, pressure and temperature. An IMS system in general includes an ion source, the drift cell, and an ion detector. The ion source ionizes molecules of a sample of interest and transmits the resulting ions into the drift cell. After traveling through the drift cell, the ions arrive at the ion detector. In low-field drift-time IMS techniques, ions travel through the drift cell under the influence of a uniform DC voltage gradient established by electrodes of the drift cell. While the electric field moves the ions through the drift cell, the ions experience a drag force due to collisions with the stationary buffer gas molecules in the drift cell. The drag force acts against the electrical force that moves the ions. The drag force experienced by an ion depends on its collision cross section (CCS or $\Omega$), which is a function of the ion's size and shape (conformation), and on its electrical charge and (to a lesser extent) mass. Ions with larger CCSs are retarded more easily by collisions with the buffer gas. On the other hand, multiply charged ions move through the buffer gas more effectively than singly charged ions because multiply charged ions experience a greater force due to the electrical field. The different CCSs of the separated ions can be correlated to their differing gas-phase mobilities through the buffer gas by the well-known Mason-Schamp equation.

Moreover, the different drift times of the separated ions through the length of the drift cell can be correlated to their differing mobilities. As the separated ions arrive at the ion detector, the ion detector counts the ions and measures their arrival times. The ion detector outputs measurement signals to electronics configured for processing the output signals as needed to produce a user-interpretable drift spectrum. The drift spectrum is typically presented as a plot containing a series of peaks indicative of the relative abundances of detected ions as a function of their drift time through the drift cell. The drift spectrum may be utilized to identify and distinguish different analyte species of the sample.

IMS may be coupled with one or more other types of separation techniques to increase compound identification power, such as gas chromatography (GC), liquid chromatography (LC), or mass spectrometry (MS). For example, an IMS drift cell may be coupled in-line with an MS system to form a combined IM-MS system. An MS system in general includes a mass analyzer for separating ions based on their differing mass-to-charge ratios (or m/z ratios, or more simply "masses"), followed by an ion detector. An MS analysis produces a mass spectrum, which is a series of peaks indicative of the relative abundances of detected ions as a function of their m/z ratios. The mass spectrum may be utilized to determine the molecular structures of components of the sample. An IM drift cell is often coupled to a time-of-flight mass spectrometer (TOFMS), which utilizes a high-resolution mass analyzer (TOF analyzer) in the form of an electric field-free flight tube. An ion extractor (or pulser) injects ions in pulses (or packets) into the flight tube. Ions of differing masses travel at different velocities through the flight tube and thus separate (spread out) according to their differing masses, enabling mass resolution based on time-of-flight.

In a combined IM-MS system, the ion source is followed by the IM drift cell, which in turn is followed by the mass analyzer and then the ion detector. Thus, ions are separated by mobility prior to being transmitted into the MS where they are then mass-resolved. Performing the two separation techniques in tandem is particularly useful in the analysis of complex chemical mixtures, including biopolymers such as polynucleotides, proteins, carbohydrates and the like. For example, the added dimension provided by the IM separation may help to separate ions that are different from each other but present overlapping mass peaks. The data acquired from processing a sample through an IM-MS system may be multi-dimensional, typically including ion abundance, acquisition time (or retention time), ion drift time through the IM drift cell, and m/z ratio as resolved by the MS. This hybrid separation technique may be further enhanced by coupling it with LC, thus providing an LC-IM-MS system.

Overlapping (or intermingling) between sequentially adjacent ion packets in the IM drift cell or TOF flight tube occurs when the slower ions of one ion packet are overtaken by faster ions of a subsequently injected ion packet. Consequently, ions from different ion packets arrive at the ion detector at the same instant of time, even though such ions have different mobilities and/or m/z ratios. The resulting measurement data acquired by the ion detector are convoluted, making the drift spectra and/or mass spectra difficult to interpret. Conventionally, this problem is avoided by operating IMS and TOFMS systems according to a "pulse and wait" approach, in which the injection rate of ion packets into the IM drift cell or the TOF flight tube is kept low enough to avoid overlapping. For example, after injecting an ion packet, the next ion packet may not be injected until the first ion packet has reached the ion detector. The pulse and wait approach thus suffers from a low duty cycle, as well as excessive ion losses between injections (at the ion gate preceding the IM drift tube or the ion pulser preceding the TOF flight tube) and thus low instrument sensitivity, particularly when a continuous-beam ion source is utilized.

Multiplexing (multiplexed injection) techniques are being developed as an improvement over the pulse and wait approach. With multiplexing, also known as over-pulsing, the injection of ion packets into the IM drift cell or the TOF flight tube is done at a high enough rate that multiple ion packets are present in the IM drift cell or TOF flight tube at the same time. Multiplexing causes overlapping between ion packets. However, multiplexing techniques address the problem of convoluted measurement data by applying some form of a deconvolution (or demultiplexing) process to the measurement data, thereby enabling a single drift time spectrum or TOF spectrum to be recovered from the measurement data. Of particular interest are deconvolution techniques based on the Hadamard transform (HT), although other types of transforms may alternatively be utilized. As an example of a HT technique, the ion packets are injected according to a pseudo-random sequence (PRS) of binary 1's and 0's, where the 1's correspond to "gate-open" (injection) events and the 0's correspond to "gate-closed" periods of time. The PRS is then used to generate an N×N Hadamard matrix, where N is the number of binary elements of the PRS. The Hadamard matrix in turn is used to generate an inverse Hadamard matrix. The inverse Hadamard matrix is then applied to the convoluted measurement data to extract a single array (or vector) of data from which a single, deconvoluted (or demultiplexed) spectrum may be generated.

One problem observed in the application of transform-based deconvolution techniques is the presence of noise in the raw measurement data to be deconvoluted, and/or residual noise in the deconvoluted measurement data (i.e., after deconvolution has been performed on the raw data). These noise components can cause inaccuracies in the deconvoluted data and subsequently generated spectra. Therefore, there is a need for IMS, TOFMS, and IM-TOFMS systems, and data acquisition methods for IMS, TOFMS, and IM-TOFMS, that reduce or eliminate noise prior to and/or after performing deconvolution.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a method for acquiring ion measurement data from a sample includes: acquiring raw measurement data from ions produced from the sample; and removing noise from the raw measurement data.

According to another embodiment, a method for acquiring ion measurement data from a sample includes: acquiring raw measurement data from ions produced from the sample; deconvoluting the raw measurement data to produce deconvoluted measurement data; and removing noise from the raw deconvoluted measurement data.

According to another embodiment, a method for acquiring ion measurement data from a sample includes: acquiring raw measurement data from ions produced from the sample; removing noise from the raw measurement data to produce modified measurement data; deconvoluting the modified measurement data to produce deconvoluted measurement data; and removing noise from the deconvoluted measurement data.

According to another embodiment, a method for acquiring ion measurement data from a sample includes: acquiring raw measurement data from ions produced from the sample; and removing noise from the raw measurement data by: arranging the raw measurement data into an array of data points, the array comprising a plurality of columns and a plurality of rows; for each row, counting a total number of positive data points contained in the row, and determining whether the total number of positive data points is less than a threshold value, wherein: if the total number of positive data points is less than the threshold value, then setting all data points in the row to zero; and if the total number of positive data points is greater than or equal to the threshold value, then retaining all data points in the row.

According to another embodiment, a method for acquiring ion measurement data from a sample includes: acquiring raw measurement data from ions produced from the sample; deconvoluting the raw measurement data to produce deconvoluted measurement data; and removing noise from the raw deconvoluted measurement data by: arranging the deconvoluted measurement data into an array of data points, the array comprising a plurality of columns and a plurality of rows; for each row, calculating a row sum of all data points in the row; finding all peaks in the row using a moving window; for each peak found, calculating a window sum of all data points in the window that includes the peak; sorting the found peaks in descending order by the window sum; for the first peak in the descending order, deducting the window sum for that peak from the row sum to obtain a new value for the row sum; for the next peak in the descending order, deducting the window sum for that peak from the new value for the row sum to obtain another new value for the row sum; repeating the deducting step for additional peaks in the descending order until the row sum value is close to zero, then stopping the deducting step; for each peak subjected to the deducting step, retaining all data points of the peak; and for each peak not subjected to the deducting step, setting all data points of the peak to zero.

According to another embodiment, a spectrometry system is configured for performing all or part of any of the methods disclosed herein.

According to another embodiment, a spectrometry system includes: an ion analyzer; an ion detector configured for receiving ions from the ion analyzer; and a computing device configured for receiving ion measurement data from the ion detector and performing all or part of any of the methods disclosed herein.

According to another embodiment, a system for acquiring spectral data from a sample includes: a processor and a memory configured for performing all or part of any of the methods disclosed herein.

According to another embodiment, a computer-readable storage medium includes instructions for performing all or part of any of the methods disclosed herein.

According to another embodiment, a system includes the computer-readable storage medium.

According to various embodiments, a spectrometry system as disclosed herein may be ion mobility spectrometry (IMS) system, a time-of-flight mass spectrometry (TOFMS) system, or a hybrid ion mobility time-of-flight mass spectrometry (IM-TOFMS) system.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

As used herein, unless specified otherwise or the context dictates otherwise, the term "spectrometry" generally may refer to ion mobility spectrometry (IMS), mass spectrometry (MS) and particularly time-of-flight mass spectrometry (TOFMS), and hybrid ion mobility-mass spectrometry (IM-MS) and particularly ion mobility time-of-flight mass spectrometry (IM-TOFMS).

As used herein, unless specified otherwise or the context dictates otherwise, the term "ion analyzer" generally may refer to a mass analyzer (particularly a TOF analyzer) or an ion mobility drift cell.

Figure 1A:
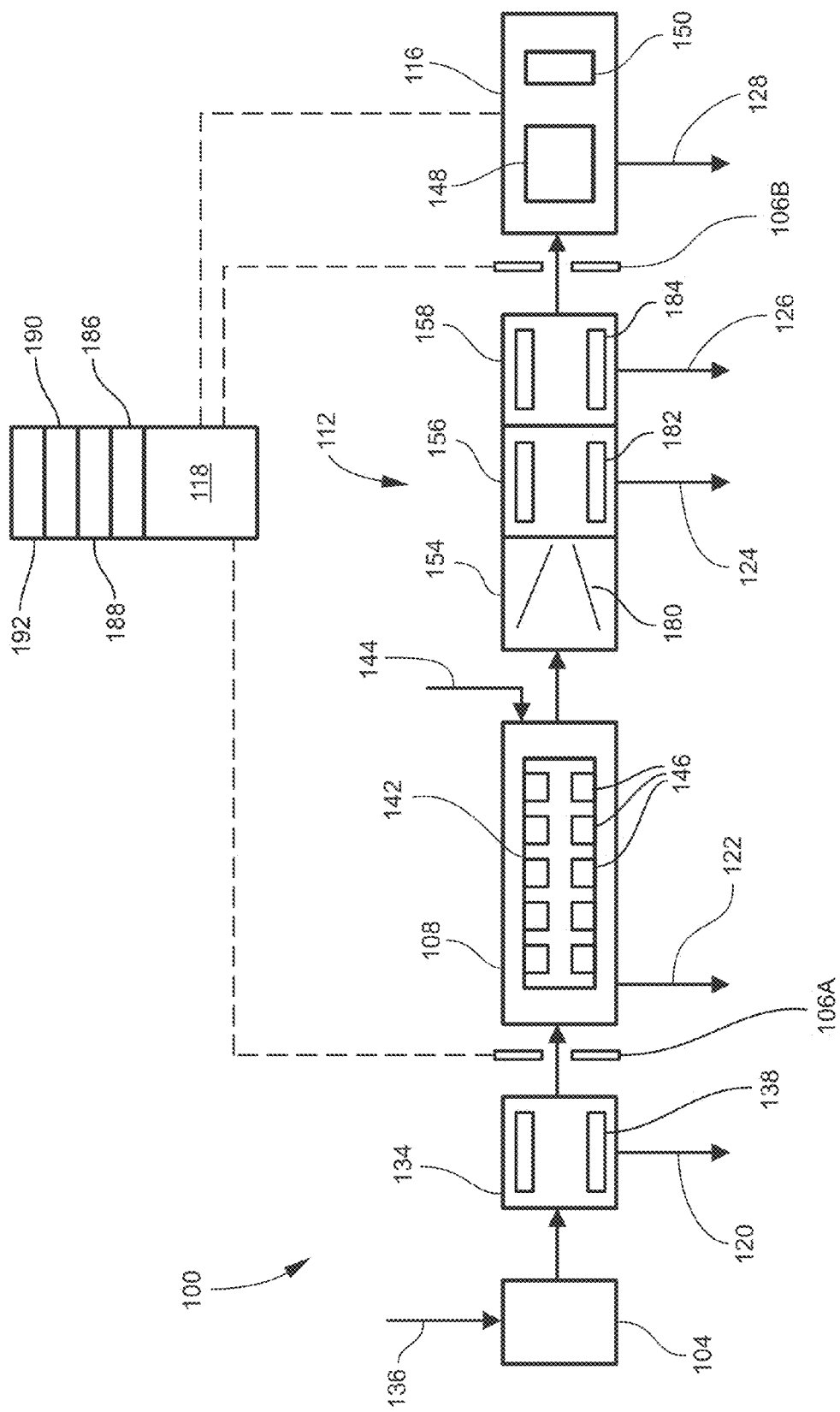
FIG. 1A is a schematic view of an example of a spectrometry system according to some embodiments, and which may be utilized in the implementation of the subject matter described herein.

FIG. 1A is a schematic view of an example of a spectrometry system 100 according to some embodiments, which may be utilized in the implementation of the subject matter described herein. The spectrometry system 100 may be an ion mobility spectrometry (IMS) system, a time-of-flight mass spectrometry (TOFMS) system, or a hybrid ion mobility time-of-flight mass spectrometry (IM-TOFMS) system. The operation and design of various components of such spectrometry systems are generally known to persons skilled in the art and thus need not be described in detail herein. Instead, certain components are briefly described to facilitate an understanding of the subject matter presently disclosed. By example, the spectrometry system 100 specifically illustrated in FIG. 1A is described as an IM-TOFMS system. Persons skilled in the art will readily recognize how the description of the IM-TOFMS system may be modified so as to apply to an IMS system or a TOFMS system.

The spectrometry system 100 may generally include an ion source 104, an ion mobility (IM) device 108, and a time-of-flight mass spectrometer (TOFMS) 116. The TOFMS 116 may be considered as including or communicating with an ion detector 150. The spectrometry system 100 also includes an ion gate 106 (106A or 106B) between the ion source 104 and the ion detector 150. In some embodiments, the ion gate 106 may be positioned just upstream of the IM device 108. This position is schematically depicted as ion gate 106A. In other embodiments in which the IM device 108 is not included (or is not operated as a drift cell), the ion gate 106 may be positioned just upstream of, or is integrated with, the ion extractor (ion pulser) of the TOFMS 116, i.e., the device functioning to inject ion packets into the flight tube of the TOFMS 116. This position is schematically depicted as ion gate 106B. In some embodiments, the spectrometry system 100 may include a device or means for accumulating ions, such as an ion trap 134, between the ion source 104 and the TOFMS 116 (or between the ion source 104 and the IM device 108, if provided). Depending on the configuration of the ion trap 134, the ion gate 106 may be part of the ion trap 134, or may be a distinct device that is downstream from the output of the ion trap 134, as appreciated by persons skilled in the art.

The spectrometry system 100 also includes a vacuum system for maintaining various interior regions of the spectrometry system 100 at controlled, sub-atmospheric pressure levels. The vacuum system is schematically depicted by vacuum lines 120-128. The vacuum lines 120-128 are schematically representative of one or more vacuum-generating pumps and associated plumbing and other components appreciated by persons skilled in the art. The vacuum lines 120-128 may also remove any residual non-analytical neutral molecules from the ion path through the spectrometry system 100.

The ion source 104 may be any type of continuous-beam or pulsed ion source suitable for producing analyte ions for spectrometry. Examples of ion sources 104 include, but are not limited to, electrospray ionization (ESI) sources, other atmospheric pressure ionization (API) sources, photo-ionization (PI) sources, electron ionization (EI) sources, chemical ionization (CI) sources, field ionization (FI) sources, plasma or corona discharge sources, laser desorption ionization (LDI) sources, and matrix-assisted laser desorption ionization (MALDI) sources. In some embodiments, the ion source 104 may include two or more ionization devices, which may be of the same type or different type. Depending on the type of ionization implemented, the ion source 104 may reside in a vacuum chamber or may operate at or near atmospheric pressure. Sample material to be analyzed may be introduced to the ion source 104 by any suitable means, including hyphenated techniques in which the sample material is an output 136 of an analytical separation instrument such as, for example, a gas chromatography (GC) or liquid chromatography (LC) instrument (not shown). In some embodiments in which the ion source 104 is configured for outputting pulses or packets of ions, the ion source 104 may provide ion accumulating functionality in which case, at least in some embodiments, the ion trap 134 may not be included. As another alternative, the ion trap 134 may be configured for performing ionization (in-trap ionization). Thus, in some embodiments the ion source 104 and the ion trap 134 may be considered as being the same instrument.

The ion trap 134 generally may have any configuration suitable for stably accumulating ions of a desired mass range for a desired period of time, and then releasing ions upon command. The ion trap 134 may, for example, include a plurality of trap electrodes 138 enclosed in a chamber or housing. The chamber may communicate with a vacuum pump that maintains the ion trap 134 at a low pressure (e.g., 1 to 20 Torr). The trap electrodes 138 may be arranged about a trap axis and surround an interior region (trap interior) in which ions may be confined. The trap electrodes 138 are in signal communication with an appropriate voltage source, which includes a radio frequency (RF) voltage source and typically also a direct current (DC) voltage source. In response to applying an RF voltage of appropriate parameters (RF drive frequency and magnitude), and typically also a DC voltage of appropriate magnitude superposed on the RF voltage, the trap electrodes 138 are configured to generate a two-dimensional RF trapping field that confines ions of a desired mass range (m/z range) to the trap interior for a desired period of time. The ion trap 134 may be operated to accumulate ions and thereafter pulse (or eject) the ions out to the TOFMS 116 (or to the IM device 108, if provided) in ion packets. Depending on the type of ion trap 134, the ion trap 134 may eject ions by modifying the RF voltage, applying additional RF or alternating current (AC) voltages, applying a DC voltage or voltages to one or more ion optics components, etc. In some embodiments, the trap electrodes 138 may be arranged in a three-dimensional or two-dimensional quadrupole configuration, as appreciated by persons skilled in the art. In other embodiments, the trap electrodes 138 may be ring-shaped electrodes or plates with apertures that are axially spaced along the trap axis. In other embodiments, the trap electrodes 138 may be configured as an ion funnel with one or more converging cross-sections. The funnel electrodes may be ring-shaped electrodes or plates with apertures that are axially spaced along the trap axis, with the inside diameters of the ring-shaped electrodes or plate apertures successively reduced to define a converging section. The funnel electrodes alternatively may be elongated generally along the trap axis and circumferentially spaced from each other about the trap axis, but oriented such that the funnel electrodes converge toward the trap axis. The ion funnel may further include one or more diverging cross-sections and/or sections of constant cross-sectional area.

The ion gate 106 generally may have any configuration suitable for pulsing an ion beam in an on/off manner, such as by deflecting, chopping, etc. For this purpose, the ion gate 106 may include one or more ion optics components such as electrodes, lenses, meshes, grids, etc. In some embodiments, the ion gate 106 may be or include a Bradbury-Nielsen gate, the configuration and operation of which are known to persons skilled in the art. Preferably, the ion gate 106 is a fast acting device capable of "opening" and "closing" on the microsecond (μs) scale. While FIG. 1A illustrates the ion gate 106 (ion gate 106A) as a separate component, in some embodiments the ion gate 106 may be integrated with the ion trap 134 (or with an appropriately configured ion source 104). That is, the ion gate 106 may the component of the ion trap 134 (or the ion source 104) that provides the pulsed ion release function.

In one specific yet non-limiting embodiment in which the ion trap 134 is provided in the form of an ion funnel, the ion trap 134 may include a converging entrance region and a diverging/constant-diameter/converging trap region. Electrostatic grid electrodes in the trap region may be utilized to pulse ions out to the drift cell, and thus in this embodiment may serve the role of the ion gate 106. Examples of funnel-based ion traps are described in U.S. patent application Ser. No. 13/906,095, filed May 30, 2013, and titled "ION MOBILITY SPECTROMETRY-MASS SPECTROMETRY (IMS-MS) WITH IMPROVED ION TRANSMISSION AND IMS RESOLUTION," the entire content of which is incorporated by reference herein. In some embodiments the interface between the ion source 304 and the ion trap 134 may include a transfer capillary leading to a separate pre-trap, high-pressure (e.g., 2 to 30 Torr) ion funnel (not shown). The high-pressure ion funnel may be oriented non-coaxially with the ion trap 134, with the axis of the high-pressure ion funnel being offset from or at an angle to that of the ion trap 134. This configuration may be useful for reducing the amount of neutral species entering the trap region and improving ion transmission into the trap region, as further described in U.S. Pat. No. 8,324,565, the entire content of which is incorporated by reference herein.

The IM device 108 may generally include an IM drift cell (or drift tube) 142 enclosed in a chamber. The chamber communicates with a vacuum pump that maintains the drift cell 142 at a buffer gas (drift gas) pressure ranging from, for example, 1 to 760 Torr. A gas inlet 144 directs an inert buffer gas (e.g., nitrogen) into the drift cell chamber. The drift cell 142 includes a series of drift cell electrodes 146 (typically ring-shaped) spaced along the axis. The drift cell electrodes 146 are in signal communication with a voltage source to generate a DC voltage gradient (e.g., 10 to 20 V/cm) along the axis. As noted above, the axial DC voltage gradient moves the ions through the drift cell 142 in the presence of the buffer gas, whereby the ions become separated in time and space based on their different mobilities through the buffer gas. The DC voltage gradient may be generated in a known manner, such as by applying a voltage between the first and last drift cell electrodes 146, and through a resistive divider network between the first and last drift cell electrodes 146, such that successively lower voltages are applied to the respective drift cell electrodes 146 along the length of the drift cell 142.

The TOFMS 116 may generally include a TOF mass analyzer 148 and an ion detector 150 enclosed in a housing. The vacuum line 128 maintains the interior of the TOFMS 116 at very low (vacuum) pressure (e.g., ranging from $10^{-4}$ to $10^{-9}$ Torr). The mass analyzer 148 separates analyte ions on the basis of their different mass-to-charge (m/z) ratios as derived from their different times-of-flight. The mass analyzer 148 includes an ion pulser (or extractor) and an electric field-free flight tube. Entrance optics direct the ion beam into the ion pulser, which pulses the ions into the flight tube as ion packets. The ions drift through the flight tube toward the ion detector 150. Ions of different masses travel through the flight tube at different velocities and thus have different overall times-of-flight, i.e., ions of smaller masses travel faster than ions of larger masses. Each ion packet spreads out (is dispersed) in space in accordance with the time-of-flight distribution. The ion detector 150 detects and records the time that each ion arrives at (impacts) the ion detector 150. A data acquisition process of the computing device 118 correlates the recorded times-of-flight with m/z ratios. The ion detector 150 may be any device configured for collecting and measuring the flux (or current) of mass-discriminated ions outputted from the mass analyzer 148. Examples of ion detectors 150 include, but are not limited to, multi-channel plates, electron multipliers, photomultipliers, and Faraday cups. In some embodiments, the ion pulser accelerates the ion packets into the flight tube in a direction orthogonal to the direction along which the entrance optics transmit the ions into the ion pulser, which is known as orthogonal acceleration TOF (oa-TOF). In this case, the flight tube often includes an ion mirror (or reflectron) to provide a 180° reflection or turn in the ion flight path for extending the flight path and correcting the kinetic energy distribution of the ions.

In some embodiments, the spectrometry system 100 may also include an ion processing section 112 generally serving as an interface (or an intermediate section or region) between the IM device 108 and the TOFMS 116, i.e., between the exit of the IM drift cell 142 and the entrance of the mass analyzer 148. Generally, the ion processing section 112 may be considered as being configured for receiving the ions eluting from the drift cell 142 and transferring the ions to the TOFMS 116. The ion processing section 112 may include one or more components (structures, devices, regions, etc.) positioned between the drift cell 142 and the TOFMS 116. These components may serve various functions such as, for example, pressure reduction, neutral gas removal, ion beam focusing/guiding, ion filtering/selection, ion fragmentation, etc. The ion processing section 112 may include a housing enclosing one or more chambers. Each chamber may include one or more such components. Each chamber may be fluidly isolated from the other chambers and provide an independently controlled pressure stage, while appropriately sized apertures are provided at the boundaries between adjacent chambers to define a pathway for ions to travel through the ion processing section 112 from one chamber to the next chamber. Any of the chambers may include one or more ion guides, such as a linear multipole ion guide (e.g., quadrupole, hexapole, octopole, etc.) or an ion funnel. Ion optics (not shown) may be provided between adjacent ion guides or other components, and may form a part of the boundary between adjacent chambers. The exact combination of components and distinct chambers making up the ion processing section 112 may vary from one TOFMS system design to another.

By way of example, in the illustrated embodiment the ion processing section 112 includes a front (or first) chamber 154, a middle (or second) chamber 156, and a rear (or third) chamber 158. In some embodiments, the front chamber 154 includes an ion funnel 180 and the middle chamber 156 and rear chamber 158 include respective multipole ion guides 182 and 184. The ion funnel 180 receives and focuses ions eluting from the IM drift cell 142. The funnel electrodes generate an RF (or composite RF/DC) ion confining field that constrains the radial component of the ion trajectories, thereby compressing the ions eluted from the IM drift cell 142 into a narrow beam along the funnel axis. The funnel electrodes may also generate an axial DC voltage gradient to keep the ions moving toward and into the next ion guide and prevent ion stalling. In some embodiments, the ion funnel 180 may be followed by one or more ion guides (not shown) in one or more additional chambers (not shown) that serve as successive pressure-reducing stages. Such a configuration is described in above-referenced U.S. patent application Ser. No. 13/906,095. The first multipole ion guide 182 in the second chamber 156 and the second multipole ion guide 184 in the third chamber 158 may each include a plurality of guide electrodes elongated along the axis, circumferentially spaced about the axis, and surrounding respective guide interiors. The guide electrodes generate an RF (or composite RF/DC) ion confining field that keeps the ions focused in a beam along the guide axis. Respective axial DC voltage gradients may be applied along the lengths of the first multipole ion guide 162 and the second multipole ion guide 184 to keep the ions moving toward downstream components and prevent ion stalling.

In some embodiments the TOFMS 116 in combination with the ion processing section 112 (or a portion thereof) may form a tandem MS or MS$^n$ system. As an example, the first multipole ion guide 182 may be configured as a (typically quadrupole) mass filter for selecting ions of a specific m/z ratio or m/z ratio range, and the second multipole ion guide 184 may be configured as a non-mass-resolving, RF-only collision cell for producing fragment ions. In the collision cell, ions collide with a collision gas (e.g., argon, nitrogen, helium, etc.). The gas pressure is high enough to enable ions that collide with the gas molecules (with sufficient energy) to fragment into less massive ions by the mechanism known as collision-induced dissociation (CID). Thus, in some embodiments the TOFMS system 100 may be considered as including a qTOF or QqTOF instrument.

The spectrometry system 100 may also include a computing device (or system controller) 118. The computing device 118 is schematically depicted as representing one or more modules (or units, or components) configured for controlling, monitoring and/or timing various functional aspects of the spectrometry system 100 such as, for example, the ion source 104, the ion gate 106, the IM device 108, and the TOFMS 116, as well as any vacuum pumps, ion optics, upstream LC or GC instrument, sample introduction device, etc., that may be provided in the spectrometry system 100 but not specifically shown in FIG. 1A. One or more modules (or units, or components) may be, or be embodied in, for example, a desktop computer, laptop computer, portable computer, tablet computer, handheld computer, mobile computing device, personal digital assistant (PDA), smartphone, etc. The computing device 118 may also schematically represent all voltage sources not specifically shown, as well as timing controllers, clocks, frequency/waveform generators and the like as needed for applying voltages to various components of the spectrometry system 100. The computing device 118 may also be configured for receiving the ion detection signals from the ion detector 128 and performing tasks relating to data acquisition and signal analysis as necessary to generate chromatograms, drift spectra, and mass (m/z ratio) spectra characterizing the sample under analysis. The computing device 118 may also be configured for providing and controlling a user interface that provides screen displays of spectrometric data and other data with which a user may interact. The computing device 118 may include one or more reading devices on or in which a tangible computer-readable (machine-readable) medium may be loaded that includes instructions for performing all or part of any of the methods disclosed herein. For all such purposes, the computing device 118 may be in signal communication with various components of the spectrometry system 100 via wired or wireless communication links (as partially represented, for example, by dashed lines between the computing device 118 and the MS 116, and between the computing device 118 and the ion gate 106A or 106B). Also for these purposes, the computing device 118 may include one or more types of hardware, firmware and/or software, as well as one or more memories and databases.

The computing device 118 may include one or more modules (or units, or components) configured for performing specific data acquisition or signal processing functions. In some embodiments, these modules may include an ion injection sequence generator such as a pseudorandom sequence (PRS) generator 186, and a deconvolution module 190. In some embodiments, these modules may further include a pre-deconvolution module 188, a post-deconvolution module 192, or both a pre-deconvolution module 188 and a post-deconvolution module 192. These modules are described further below.

Figure 1B:
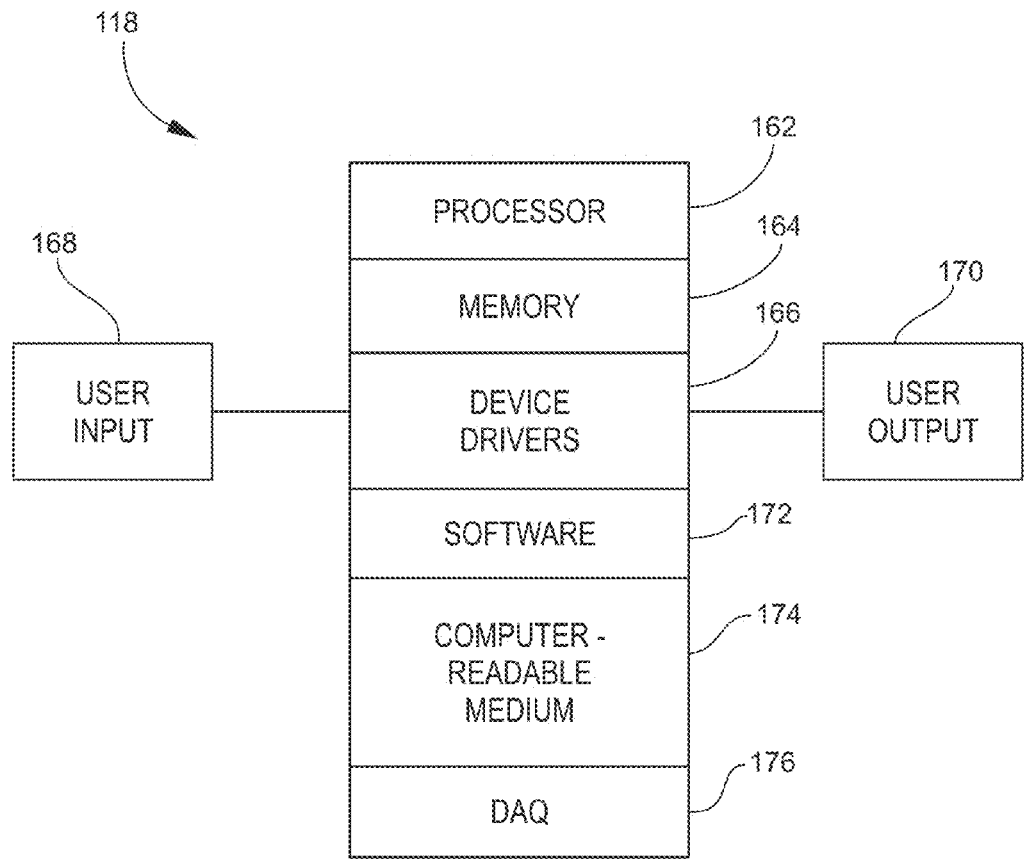
FIG. 1B is a schematic view of an example of a computing device that may be part of or communicate with the spectrometry system illustrated in FIG. 1A, according to some embodiments.

FIG. 1B is a schematic view of a non-limiting example of a computing device 118 that may be part of or communicate with a spectrometry system such as the spectrometry system 100 illustrated in FIG. 1A. In the illustrated embodiment the computing device 118 includes a processor 162 (typically electronics-based), which may be representative of a main electronic processor providing overall control, and one or more electronic processors configured for dedicated control operations or specific signal processing tasks (e.g., a graphics processing unit, or GPU). The computing device 118 also includes one or more memories 164 (volatile and/or non-volatile) for storing data and/or software. The computing device 118 may also include one or more device drivers 166 for controlling one or more types of user interface devices and providing an interface between the user interface devices and components of the computing device 118 communicating with the user interface devices. Such user interface devices may include user input devices 168 (e.g., keyboard, keypad, touch screen, mouse, joystick, trackball, and the like) and user output devices 170 (e.g., display screen, printer, visual indicators or alerts, audible indicators or alerts, and the like). In various embodiments, the computing device 118 may be considered as including one or more user input devices 168 and/or user output devices 170, or at least as communicating with them. The computing device 118 may also include one or more types of computer programs or software 172 contained in memory and/or on one or more types of computer-readable media 174. Computer programs or software may contain instructions (e.g., logic instructions) for performing all or part of any of the methods disclosed herein. Computer programs or software may include application software and system software. System software may include an operating system (e.g., a Microsoft Windows® operating system) for controlling and managing various functions of the computing device 118, including interaction between hardware and application software. In particular, the operating system may provide a graphical user interface (GUI) displayable via a user output device 170 such as a display screen, and with which a user may interact with the use of a user input device 168 such as a keyboard or a pointing device (e.g., mouse). The computing device 118 may also include one or more data acquisition/signal conditioning components 176 (as may be embodied in hardware, firmware and/or software) for receiving and processing ion measurement signals outputted by the ion detector 150, including formatting data for presentation in graphical form by the GUI. The data acquisition/signal conditioning components 176 may include signal processing modules such as the PRS generator 186, the pre-deconvolution module 188, the deconvolution module 190, and the post-deconvolution module 192 noted above and described in further detail below.

It will be understood that FIGS. 1A and 1B are high-level schematic depictions of an example of a spectrometry system 100 and associated computing device 118 consistent with the present disclosure. Other components, such as additional structures, vacuum pumps, gas plumbing, ion optics, ion guides, electronics, and computer- or electronic processor-related components may be included as needed for practical implementations. It will also be understood that the computing device 118 is schematically represented in FIGS. 1A and 1B as functional blocks intended to represent structures (e.g., circuitries, mechanisms, hardware, firmware, software, etc.) that may be provided. The various functional blocks and signal links have been arbitrarily located for purposes of illustration only and are not limiting in any manner. Persons skilled in the art will appreciate that, in practice, the functions of the computing device 118 may be implemented in a variety of ways and not necessarily in the exact manner illustrated in FIGS. 1A and 1B and described herein.

An example of the general operation of the spectrometry system 100 for acquiring spectral data from a sample will now be described. The ion source 104 ionizes a sample, forming analyte ions, and transmits the ions into the ion trap 134. The ion trap 134 accumulates the ions for a period of time (e.g., 1 ms). The ion gate 106 periodically opens momentarily (e.g., 150 µs) to inject discrete ion packets sequentially into the IM drift cell 142. Each ion packet may contain ions having a range of m/z ratios. The injection sequencing of the ion gate 106 is controlled by the computing device 118. The intervals of time between injections (when the ion gate 106 is closed) are typically on the scale of milliseconds (ms). The ion packets drift through the IM drift cell 142 under the influence of the electric field gradient (which is typically uniform and relatively weak) established by the drift cell electrodes 146. As the ion packets drift through the IM drift cell 142, collisions occur between the ions and the drift gas. Consequently, the ion packets become spread out in time and space in accordance with the mobility distribution of the ions. The ions exit the IM drift cell 142 and are transmitted into the TOFMS 116. As described above, in some embodiments the ions may be subjected to intermediate processes in an ion processing section 112 before entering the TOFMS 116, such as focusing, cooling, mass filtering or selection, fragmentation, etc.

As the ions enter the TOFMS 116, the ion pulser of the TOFMS 116 injects (pulses) the ions into the flight tube according to a sequence controlled by the computing device 118. Hence, the TOFMS 116 injects "new" ion packets into the flight tube. The ion packets injected into the flight tube are "new" in the sense that they are not the same packets as those originally injected into the IM drift cell 142. The TOF injection pulses typically occur on a much faster time scale (e.g., µs) than the IM injection pulses (e.g., ms). That is, the TOF injection rate (or frequency) is typically much higher than the IM injection rate (or frequency), such that many TOF injection pulses occur during the period between two sequential IM injection pulses. As the ion packets drift through the electric field-free region of the flight tube, the ion packets become spread out in time and space in accordance with the TOF distribution of the ions. The ion detector 150 located at the end of the flight path counts each ion impacting the ion detector 150 and measures its arrival time, and the detector output signal is digitized and recorded in a manner appreciated by persons skilled in the art. The arrival time of an ion at the ion detector 150 is a sum of the ion's drift time through the IM drift cell 142, flight time through the flight tube (TOF), and travel time through other regions of the system between the IM drift cell 142 and the flight tube. The data acquisition/signal components (schematically associated with the computing device 118 in FIGS. 1A and 1B) are configured for calculating the drift time and TOF of each ion from the measured arrival time, as well as determining m/z ratio based on TOF as noted earlier. The data acquisition/signal components are also configured for producing drift time and mass spectra from the raw measurement data (arrival times and ion counts) measured by the ion detector 150.

In the above-described operation, injection of ion packets into the IM drift cell 142 may be multiplexed such that two or more adjacent ion packets become overlapped in the IM drift cell 142 at some point in time during their travel through the IM drift cell 142. Likewise, injection of ion packets into the flight tube of the TOF mass analyzer 148 may be multiplexed such that two or more adjacent ion packets become overlapped in the flight tube at some point in time during their travel through the flight tube. The computing device 118 (or a modulating device controlling the ion gate 106 and controlled by the computing device 118) may be configured for implementing multiplexed injection into the IM drift cell 142 by controlling the opening and closing of the ion gate 106 according to an ion injection sequence. In some embodiments, the ion injection sequence is a pseudorandom sequence (PRS) of binary 1's and 0's, also known as a pseudorandom binary sequence. One of the binary states (e.g., binary 1), which may also be referred to as an ON state (or pulse) or open state (or pulse), corresponds to opening the ion gate 106 for a brief period of time (e.g., 150 μs) followed by closing the ion gate 106. The ON pulse results in an ion packet being injected into the IM drift cell 142. The other binary state (e.g., binary 0), which may also be referred to as an OFF state (or pulse) or closed state (or pulse), corresponds to closing the ion gate 106 for a period of time lasting until the next ON pulse. The present disclosure arbitrarily associates the ON state with binary 1 and the OFF state with binary 0.

The PRS generator 186 may generate the PRS, for example, through the operation of linear feedback shift registers. In some embodiments, the PRS is a maximum length sequence (MLS). An MLS-type PRS has a length $N=2^m-1$, where m is the number of bits (or shift registers) utilized to construct the PRS. As examples, a 3-bit PRS has a length $N=7$ ($2^3-1$), a 4-bit PRS has a length $N=15$ ($2^4-1$), and a 5-bit PRS has a length $N=31$ ($2^5-1$). Examples of 3-bit, 4-bit, and 5-bit PRSs are as follows:

3 bits: {0, 0, 1, 0, 1, 1, 1}
4 bits: {0, 0, 0, 1, 0, 0, 1, 1, 0, 1, 0, 1, 1, 1, 1}
5 bits: {0, 0, 0, 0, 1, 0, 0, 1, 0, 1, 1, 0, 0, 1, 1, 1, 1, 1, 0, 0, 0, 1, 1, 0, 1, 1, 1, 0, 1, 0, 1}

Figure 2:
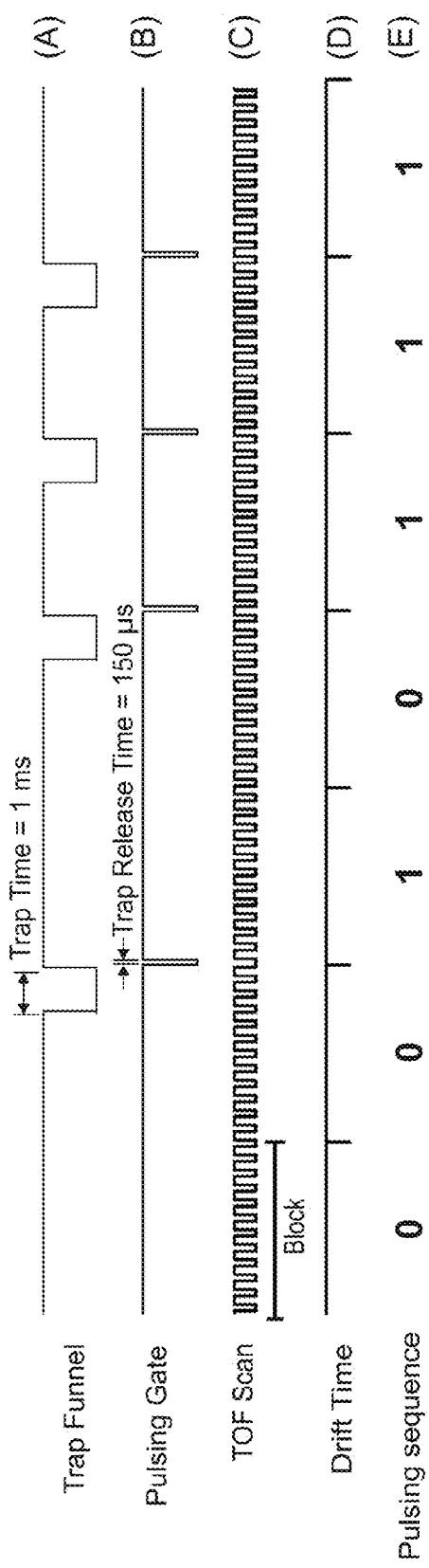
FIG. 2 illustrates an example of a set of timing sequences for operation of an ion trap (sequence A), an ion gate (sequence B), and a TOF pulser (sequence C), and also illustrates a corresponding drift time period (sequence D) and a pseudo-random sequence (PRS) applied to the ion gate (sequence E), according to some embodiments.

FIG. 2 illustrates a set of timing sequences for operation of the ion trap 134 (sequence A), ion gate 106A (sequence B), and TOF pulser (sequence C). FIG. 2 also illustrates the corresponding drift time period (sequence D) and the PRS applied to the ion gate 106A (sequence E). The PRS selected for the example in FIG. 2 is the 3-bit PRS set forth above. The total period of time over which the sequence occurs (corresponding to the overall drift time period shown in FIG. 2) may constitute a single experiment, or a single iteration that may be repeated one or more times (e.g., thousands of times) during a given experiment, as appreciated by persons skilled in the art. In the present embodiment, the (overall) drift time period is divided into drift time blocks (segments, bins, etc.) of equal duration, as indicated by sequence D. The number of drift time blocks is equal to the length N (the number of binary elements) of the PRS, which in this example is seven. Each binary element of the PRS is exclusively associated with one of the drift time blocks. Likewise, each ion trapping event and each ion gate-open (trap release, or injection) event are exclusively associated with one of the drift time blocks. Each ion trapping event is immediately followed by a gate-open event. Each ion trapping event may be of equal duration (e.g., 1 ms), and the duration is shorter than the duration of the drift time blocks (e.g., several ms each). Each gate-open event may be of equal duration (e.g., 150 μs), and the duration is likewise shorter than the duration of the drift time blocks. Each TOF injection pulse may be of equal duration (e.g., on the order of μs), and the duration is shorter than the duration of the drift time blocks. By example only, FIG. 2 shows twelve TOF injection pulses per drift time block, with the understanding that more or less TOF injection pulses may occur during each drift time block.

In the present example, the PRS begins with two successive binary 0 states. Accordingly the ion gate 106 is closed, and thus no ion packets are injected into the IM drift cell 142, during the first two drift time blocks. The first two binary 0 states are followed by a binary 1 state. Accordingly, ion trapping is initiated at or near the end of the second drift time block to accumulate ions, and the ion trapping (accumulation) period is followed by opening the ion gate 106 at the start of the third drift time block to inject an ion packet into the IM drift cell 142. As noted above, the ion gate 106 is open only for a brief period of time and thus is closed for the remaining duration of the third drift time block. The fourth drift time block is associated with binary 0, and accordingly the ion gate 106 remains closed during the entire fourth drift time block. The fifth, sixth, and seventh drift time blocks are each associated with binary 1's, and thus ion injecting events occur in each of the fifth, sixth, and seventh drift time blocks (respectively preceded by ion trapping events at the end of the fourth, fifth, and sixth drift time blocks).

Each period of time during which the ion gate 106 is open may be considered as an ON pulse. All remaining periods of time (the intervals between ON pulses) may be considered as OFF pulses. From FIG. 2, it is seen that each drift time block includes either a single ON pulse followed by an OFF pulse (when the drift time block is associated with binary 1), or no ON pulses (when the drift time block is associated with binary 0). Also, the durations of the OFF pulses included in the injection sequence are variable. This is because the duration of an OFF pulse depends on whether a binary 1 is followed by another binary 1 or by a binary 0, or by two or more successive binary 0's. Moreover, the duration of an OFF pulse may be longer than the duration of a single drift time block. For example, in FIG. 2, the third, fourth, and fifth drift time blocks are associated with the sub-sequence {1, 0, 1}. Hence, an OFF pulse extends over a portion of the third drift time block and over the entire duration of the fourth drift time block, and ends at the beginning of the fifth drift time block at which time the next ON pulse occurs. It is also seen that for a given IM device 108, the drift time blocks may be scaled as needed for the PRS applied to ion gate 106A to effect multiplexed injection, with some degree of overlapping occurring between one or more pairs of adjacent ion packets as they travel through the drift cell 142.

Due to the overlapping, at any given instant of time during the experiment, ions of differing mobility and/or m/z ratios may arrive at the ion detector 150 simultaneously. Hence, the resulting raw measurement data generated by the ion detector 150 is a measurement of several TOF distributions, each of which is shifted in time relative to the start time of the PRS, and some of which overlap with preceding and/or succeeding TOF distributions. In mathematical terms, this raw measurement data may be considered as being a convolution of a single TOF distribution and the PRS. The deconvolution module 190 may be configured for recovering the single TOF distribution by subjecting the convoluted raw measurement data to a deconvolution (or demultiplexing) process that utilizes knowledge of the particular PRS that was applied to the ion gate 106. The deconvolution process may entail the application of an appropriately designed deconvolution algorithm.

In some embodiments, the convolution may be expressed as F×G=H, where F is the TOF distribution sought to be recovered, G is a function (e.g., a transfer function, or transform) related to the applied PRS, and H is the raw measurement data. In some embodiments, the deconvolution module 190 is configured for constructing G as a transfer function (or transform), calculating the inverse $G^{-1}$ of the transfer function, and multiplying both sides of the expression F×G=H by the inverse transfer function $G^{-1}$ as follows: $G^{-1} \times (F \times G) = H \times G^{-1}$. This process yields the demultiplexed TOF distribution F, $F=H \times G^{-1}$, which may then be processed to construct drift time and mass spectra, as appreciated by persons skilled in the art. The transfer function G may be a Hadamard transform (HT) or fast Hadamard transform, or alternatively may be another type of transform utilized in signal processing and that is based on a PRS or other code utilized for multiplexing.

After deconvolution, the resulting deconvoluted measurement data are utilized to produce a drift time versus abundance spectrum, a mass versus abundance spectrum, or a drift time versus mass versus abundance spectrum, depending on whether the spectrometry system 100 is an IMS system, a TOFMS system, or an IM-TOFMS system, respectively.

As noted earlier, the raw measurement data may include noise components that cause errors or inaccuracies in the deconvoluted measurement data, in turn leading to errors or inaccuracies in the drift time and/or mass spectra constructed from the deconvoluted measurement data. According to some embodiments, a method is implemented for removing noise components from the raw measurement data prior to applying the deconvolution algorithm. The pre-deconvolution module 188 (FIG. 1A) may be configured for implementing this method. Generally, the method processes the raw measurement data to produce modified measurement data in which noise components have been eliminated. The modified measurement data may then be subjected to a deconvolution process as described above to produce deconvoluted measurement data.

Figure 3:
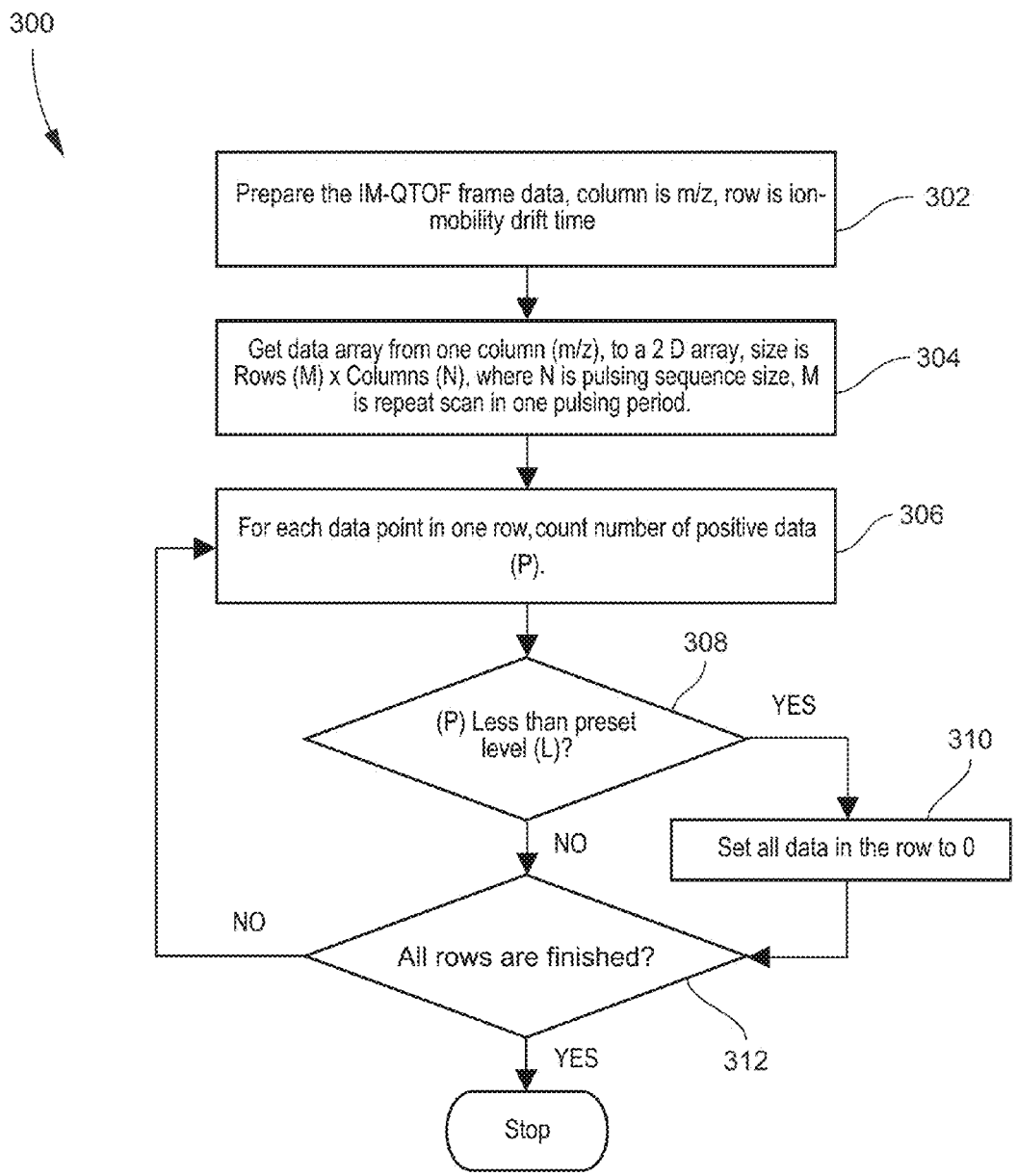
FIG. 3 is a flow diagram illustrating a method for removing noise from raw measurement data according to some embodiments.
Figure 4:
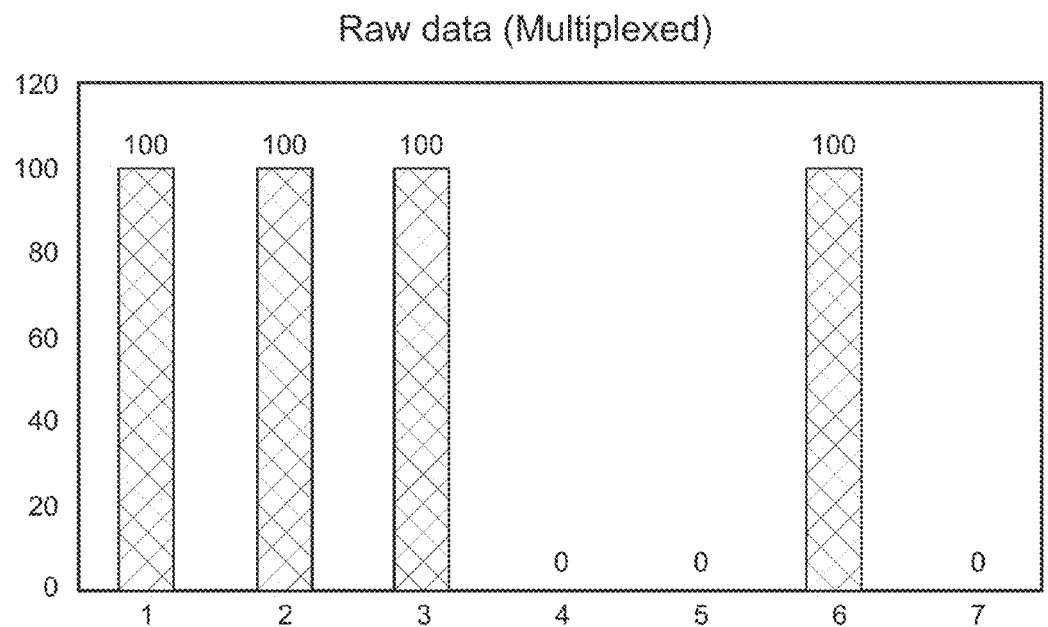
FIG. 4 illustrates one row (linear array) of a simplified example of a 2D array to which the method of FIG. 3 may be applied.
Figure 5:
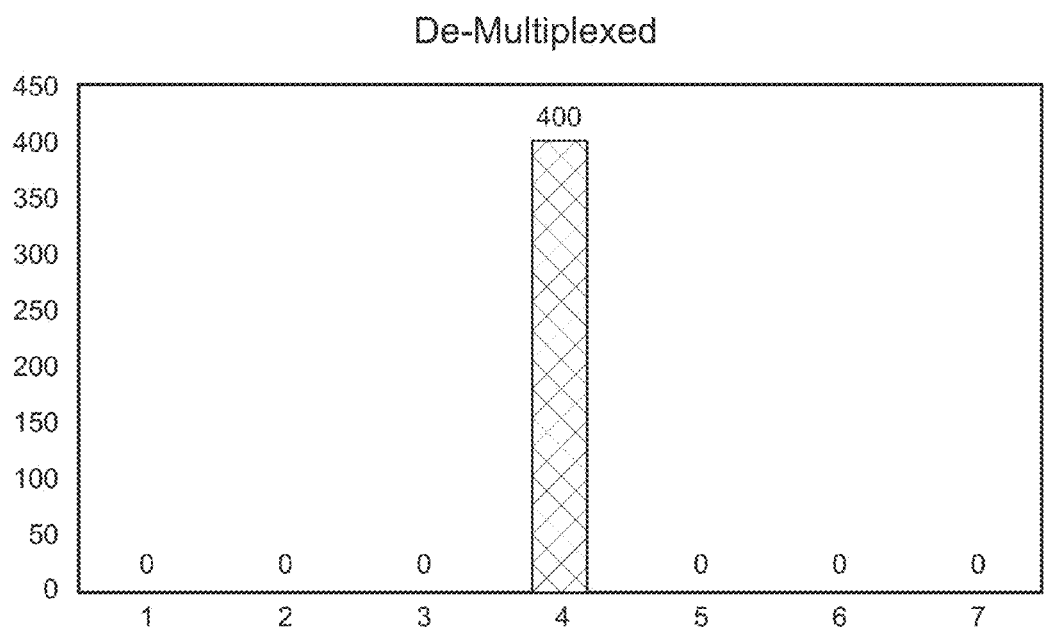
FIG. 5 illustrates an example of the row (linear array) shown in FIG. 4 after deconvolution.

A non-limiting example of the method for removing noise from raw measurement data will now be described with reference to FIGS. 3 to 5. FIG. 3 is a flow diagram 300 of the method. The flow diagram 300 may also be representative of a system, pre-deconvolution module 188, and/or computer program product configured for implementing the method. The raw measurement data is arranged in a two-dimensional (2D) N×M array of data points (step 302), where N is the number of columns and M is the number of rows of the data array. The integer value N is the size (length) of the PRS, which corresponds to the number of drift time blocks as described above. The integer value M is the number of TOF scans per drift time block (i.e., per IM injection event). The data points (abundance peaks) are signal intensity values corresponding to either abundance (ion counts) or noise. The method entails interrogating each row (linear data array) of the 2D array (step 304). FIG. 4 illustrates one row (linear array) of a simplified example of a 2D array. In this example, a 3-bit PRS was utilized, specifically {1, 1, 1, 0, 0, 1, 0}, resulting in N=7 drift time blocks across the row (horizontal axis) and thus seven data points per row, the value of each data point being plotted along the vertical axis. Consistent with the example of FIG. 2 (sequence C), twelve TOF scans occur per drift time block, and thus column M=12.

According to the method, a total number (P) of positive data points in the row are counted (step 306). In the example of FIG. 4, the row includes four positive-value data points (P=4), which for simplification each have a signal intensity value of 100. A determination is then made (step 308) as to whether the number P is less than a predetermined threshold (or minimum) level (L). If P is less than L, the data point(s) of the row are assumed to be noise, and all data points in this row are set to zero (step 310). If, on the other hand, P is equal to or greater than L, all data points in this row are retained in the 2D array. Thus, in the example of FIG. 4, assuming L has been set to two (L=2), this row of data would be retained because the number of positive data points contained in this row satisfies the criterion, i.e., P is greater than L (4>2) or, stated differently, P is not less than L.

After determining for the current row whether P is less than L (step 308) and, if applicable, zeroing out the row (step 310), a determination is then made as to whether all rows have been interrogated in this manner (step 312). If not, then steps 306 to 312 are repeated as described above. The method continues until each row has been interrogated, and then stops. The output of the method is modified measurement data in which noise that was originally part of the raw measurement data inputted into the method has now been removed. The modified measurement data may then be subjected to a deconvolution process as described above to produce deconvoluted measurement data. FIG. 5 illustrates an example of the row (linear array) shown in FIG. 4 after deconvolution. FIG. 5 illustrates an ideal case in which the row contains no noise.

In practice, deconvoluted measurement data often contain noise components. According to some embodiments, a method is implemented for removing noise components from deconvoluted measurement data. The post-deconvolution module 192 (FIG. 1A) may be configured for implementing this method. Generally, the method processes the deconvoluted measurement data to produce modified deconvoluted measurement data in which noise components have been eliminated. The modified deconvoluted measurement data may then be utilized to produce drift time and/or mass spectra as described above.

Figure 6:
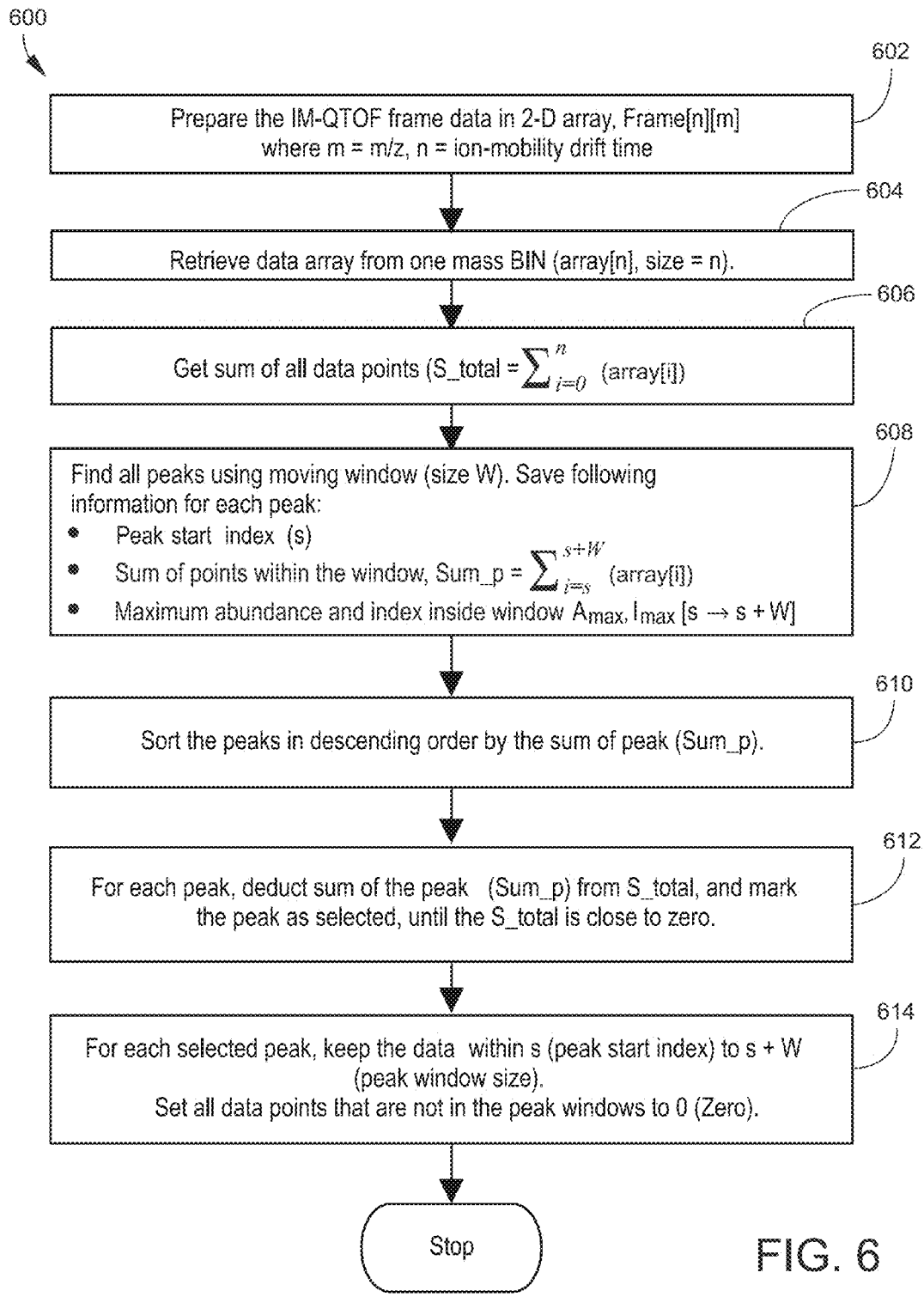
FIG. 6 is a flow diagram illustrating a method for removing noise from deconvoluted measurement data according to some embodiments.
Figure 7:
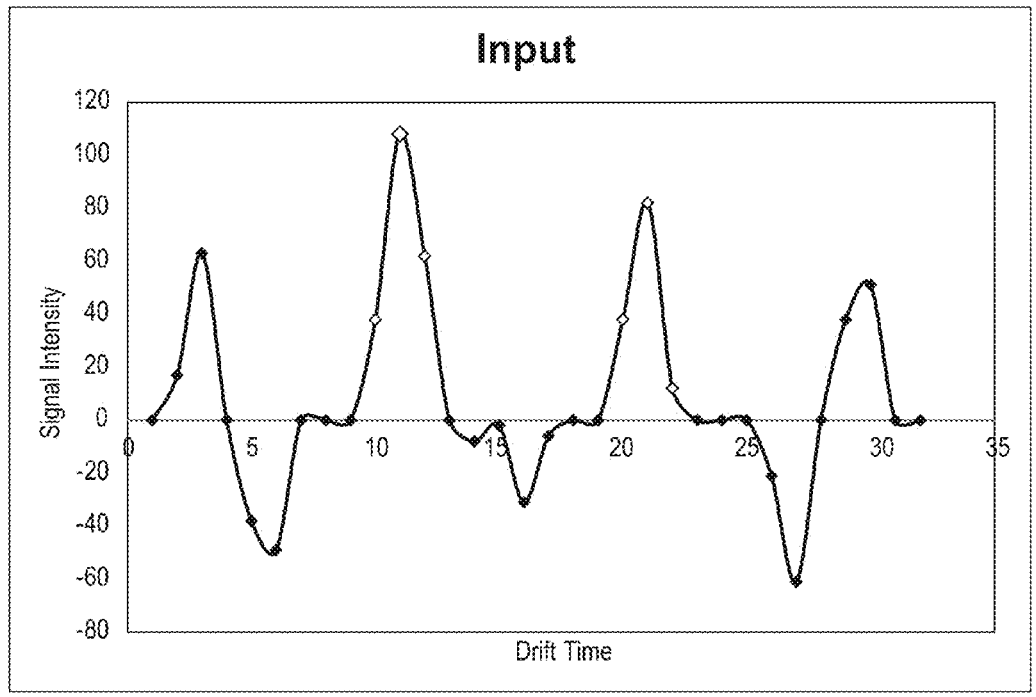
FIG. 7 illustrates one row (linear array) of a simplified example of a 2D array to which the method of FIG. 6 may be applied.

A non-limiting example of the method for removing noise from deconvoluted measurement data will now be described with reference to FIGS. 6 to 9. FIG. 6 is a flow diagram 600 of the method. The flow diagram 600 may also be representative of a system, post-deconvolution module 192, and/or computer program product configured for implementing the method. Raw measurement data is acquired and deconvoluted according to any of the embodiments described herein. The resulting deconvoluted measurement data is arranged in a two-dimensional (2D) N×M array of data points (step 602), where N is the number of columns and M is the number of rows of the data array. The integer value N is the size (length) of the PRS, which corresponds to the number of drift time blocks (or indices) as described above. The integer value M is the number of TOF scans per drift time block (index) (i.e., per IM injection event). The data points are signal intensity values corresponding to either abundance (ion counts) or noise. The method entails interrogating each row (linear data array[N]) of the 2D array (step 604). FIG. 7 illustrates one row (linear array) of a simplified example of a 2D array. In this example, a 5-bit PRS was utilized, resulting in N=31 drift time blocks across the row (horizontal axis) and thus thirty-one data points per row, the value of each data point being plotted along the vertical axis. Consistent with the example of FIG. 2 (sequence C), twelve TOF scans occur per drift time block, and thus column M=12. The TABLE below provides the data point values for the row ("Input Array") shown in FIG. 7.

TABLE

| Index | Input Array | Output Array |
|---|---|---|
| 0 | 0 | 0 |
| 1 | 17 | 0 |
| 2 | 63 | 0 |
| 3 | 0 | 0 |
| 4 | −38 | 0 |
| 5 | −49 | 0 |
| 6 | 0 | 0 |

TABLE-continued

| Index | Input Array | Output Array |
|---|---|---|
| 7 | 0 | 0 |
| 8 | 0 | 0 |
| 9 | 38 | 38 |
| 10 | 108 | 108 |
| 11 | 62 | 62 |
| 12 | 0 | 0 |
| 13 | −8 | 0 |
| 14 | −2 | 0 |
| 15 | −31 | 0 |
| 16 | −6 | 0 |
| 17 | 0 | 0 |
| 18 | 0 | 0 |
| 19 | 38 | 38 |
| 20 | 82 | 82 |
| 21 | 12 | 12 |
| 22 | 0 | 0 |
| 23 | 0 | 0 |
| 24 | 0 | 0 |
| 25 | −21 | 0 |
| 26 | −61 | 0 |
| 27 | 0 | 0 |
| 28 | 38 | 0 |
| 29 | 51 | 0 |
| 30 | 0 | 0 |
| 31 | 0 | 0 |

According to the method, the sum of all data points in the row (including negative values), S_Total (or "row sum"), is calculated (step 606):

$$S_{Total} = \Sigma_{i=0}^{N}(array[i])$$

where N is the size of the array, and i is the index (integer value) of each successive column of the array (i=0, 1, 2, 3, . . . ).

In the example of FIG. 7 (and above TABLE), S_Total is 293.

Next, all peaks in the row are found with the use of a moving window of predefined window size W (step 608). The start index and end index of the window may be expressed as (i, i+W), where i=0, 1, 2, 3, . . . . For each iteration of moving the window, the window is shifted by one index value. Thus, for a window of size W=5, the first window has a start index and end index of (0, 5), the next window has a start index and end index of (1, 6), and so on. For each peak found, the following information is then saved:

The index number (s) corresponding to the start (the first data point) of the peak;

For the largest data point inside each window (the data point having the maximum abundance), the data point value of that maximum abundance, Amax, and the index of that (largest) data point, $I_{max}$ [s→s+W]; and For each window, the sum of data points (Sum_p, or "window sum") in that window:

$$Sum_p = \Sigma_{i=s hu\ s+W}(array[i]).$$

In the example of FIG. 7, using a window size W=5, two peaks are found, Peak 1 and Peak 2. Peak 1 starts at I=9. The maximum abundance of Peak 1 is 108. The sum of the data points of Peak 1 is Sum_p=108+38+62=208. Peak 2 starts at I=19. The maximum abundance of Peak 2 is 82. The sum of the data points of Peak 2 is Sum_p=82+38+12=132.

Next, the peaks are sorted in descending order (step 610) by their respective row sums (Sum_p). In the example of FIG. 7, the first peak of the descending order would be Peak 1 (Sum_p=208), and the next peak in the descending order would be Peak 2 (Sum_p=132).

Next, a loop process is initiated (step 612). For the first peak of the descending order, its row sum (Sum_p) is deducted from the sum of all data points in the row (S_Total) to obtain a new total sum value (S_Total): S_Total=S_Total−Sum_p. For the second peak of the descending order, its row sum (Sum_p) is deducted from the new total sum value (S_Total) calculated from the previous iteration, to obtain a new total sum value (S_Total): S_Total=S_Total−Sum_p. The process is repeated for all subsequent peaks of the descending order, each time deducting the row sum (Sum_p) of the peak from the total sum value (S_Total) obtained from the preceding iteration. The process is repeated until the total sum value (S_Total) is close to zero, and then the loop process stops. In the example of FIG. 7, the first iteration S_Total=S_Total−Sum_p is carried out for Peak 1: 293−208=85. Using this new S_Total value (85), the next iteration S_Total=S_Total−Sum_p is carried out for Peak 2: 85−132=−47. In the example of FIG. 7, the process stops after Peak 2 as there are no more peaks.

Figure 8:
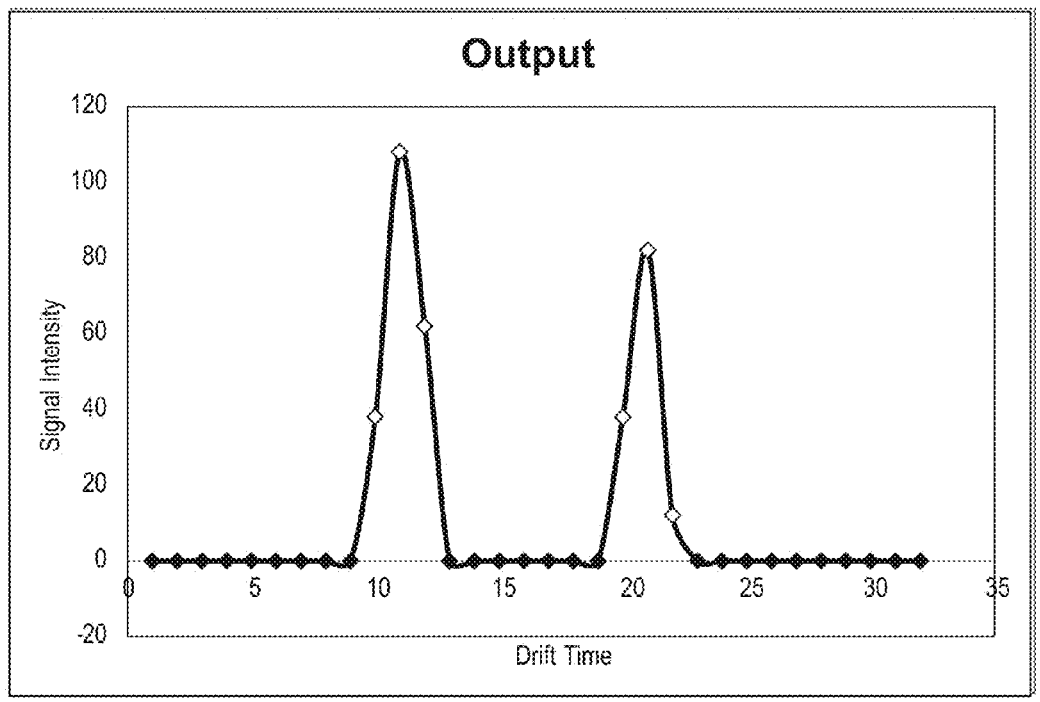
FIG. 8 illustrates an example of the row (linear array) shown in FIG. 7 after applying the method of FIG. 6.

Next, for all of the peaks subjected to the loop process before the process was stopped, these peaks are selected to be retained in the data array (step 614). That is, for each selected peak, all of the data points within the peak, from s (peak start index) to s+W (peak window size) are retained. All other data points (all data points that are not in the peak windows) are set to zero. In the example of FIG. 7, Peak 1 and Peak 2 are retained. FIG. 8 illustrates the result of retaining Peak 1 and Peak 2 and zeroing out all other data points in the data array of FIG. 7. It is seen that the noise components have been removed. The TABLE above provides the data point values for the row ("Input Array") shown in FIG. 8.

The foregoing method may be repeated for all other rows of the 2D array.

The output of the foregoing method, referred to as modified deconvoluted measurement data, may then be utilized to produce drift time and/or mass spectra as described above.

Figure 9:
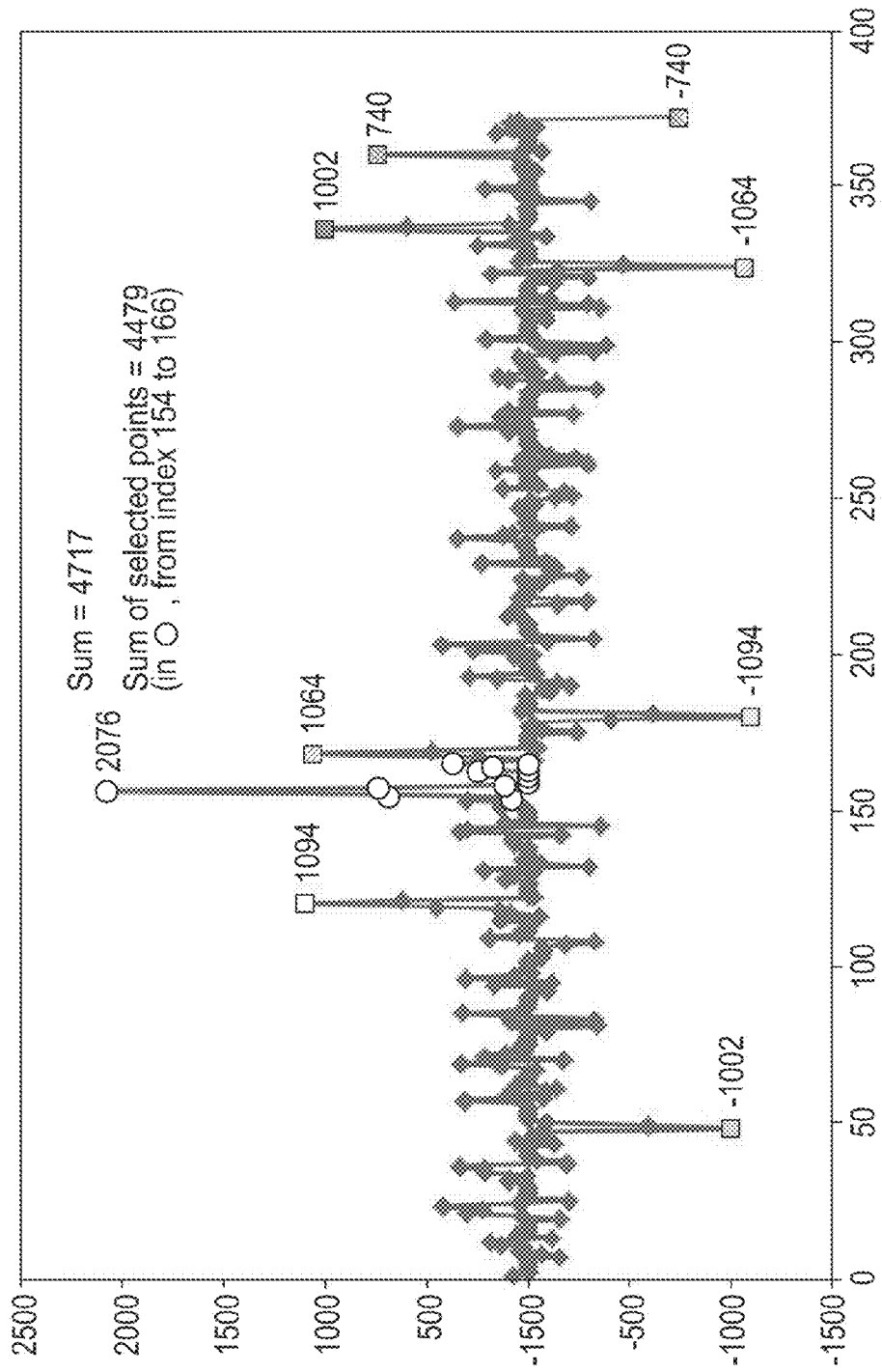
FIG. 9 is an example of a drift spectrum to which the method of FIG. 6 may be applied.
Figure 10:
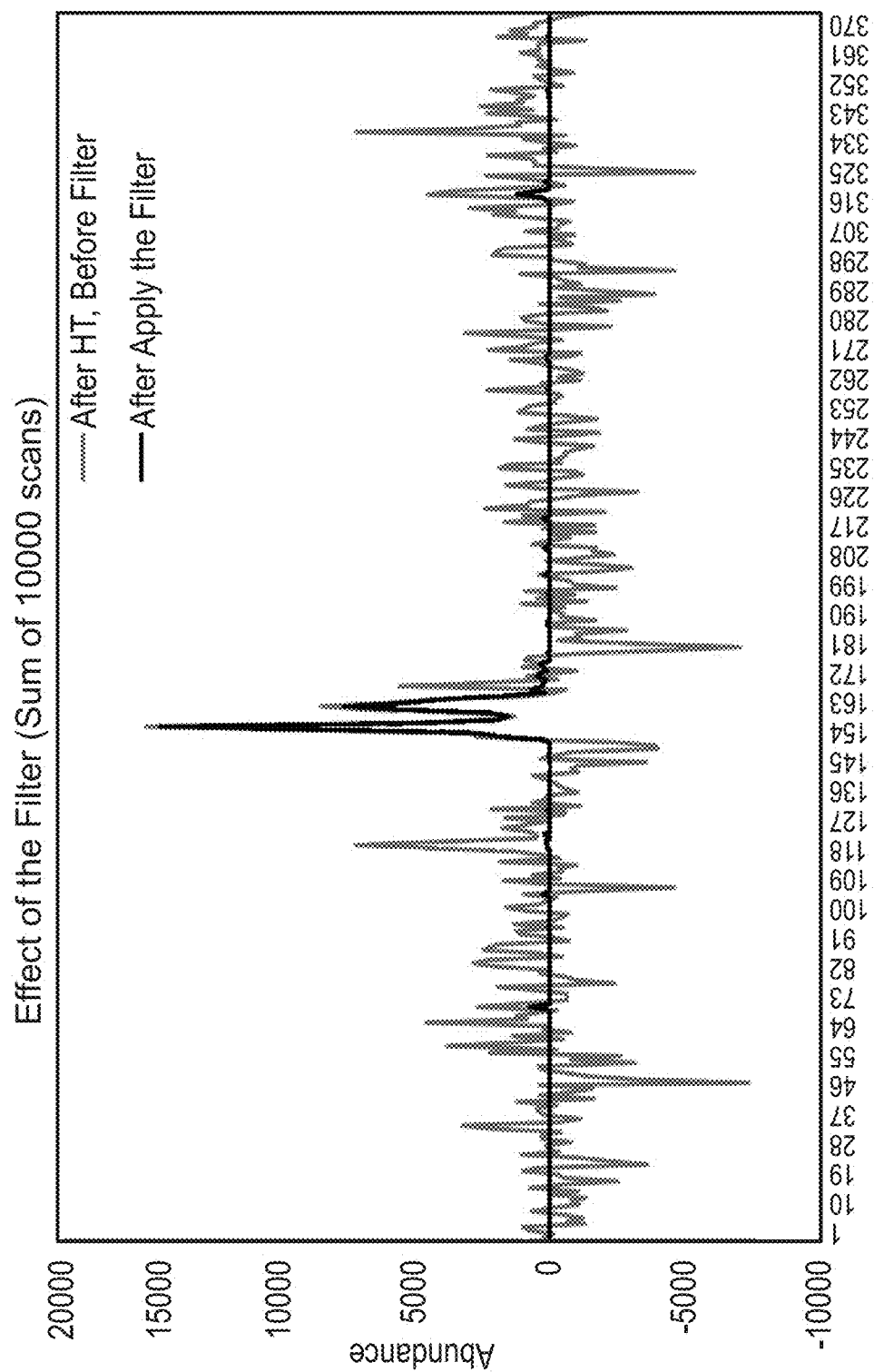
FIG. 10 is an example of the drift spectrum of FIG. 9 after summing 10,000 scans, before the method of FIG. 6 is applied (lighter trace) and after the method of FIG. 6 is applied (darker trace).

FIG. 9 is an example of a single drift spectrum to which the post-deconvolution noise reduction method described above may be applied. The sum of all data points is 4717. Using the method, one peak is found. The peak includes data points from indices 154 to 166, which sum to 4479. It is seen that the noise peaks are symmetrical (−740 and 740, −1002 and 1002, −1064 and 1064, and −1094 and 1094). FIG. 10 is an example of the drift spectrum of FIG. 9 after summing 10,000 scans, before the post-deconvolution noise reduction method is applied (lighter trace) and after the method of FIG. 6 is applied (darker trace). It is seen that the method filters out the noise peaks.

In various embodiments, the pre-deconvolution method for removing noise may be implemented without also implementing the post-deconvolution method for removing noise, or the post-deconvolution method may be implemented without also implementing the pre-deconvolution method, or both the pre-deconvolution method and the post-deconvolution method may be implemented. As an example of the latter case, the pre-deconvolution method may be carried out to remove noise from raw measurement data, and the resulting modified raw measurement data may be deconvoluted to produce deconvoluted measurement data. This set of deconvoluted measurement data may still include noise, which may be removed by carrying out the post-deconvolution method on this set of deconvoluted measurement data. Thus in some embodiments, performing both the pre-deconvolution method and the post-deconvolution method may be useful for removing noise by way of two different techniques, and may be more effective than performing just one of the methods.

In various embodiments, the pre-deconvolution method and/or the post-deconvolution method may be implemented as part of a method for acquiring spectral data from a sample that entails multiplexing and deconvolution.

From the foregoing description, it will be appreciated by persons skilled in the art that the spectrometry system 100 schematically illustrated in FIG. 1A may be reconfigured as an IMS system (e.g., by replacing the TOFMS 116 with a suitable non-mass resolving ion detector) or as a TOFMS system (e.g., by removing the IM device 108, or by operating the IM device 108 as an ion transfer device without a significant buffer gas pressure). From the foregoing description, it will also be appreciated by persons skilled in the art how the pre-deconvolution and post-deconvolution methods may be implemented in the context of an IMS system or a TOFMS system.

Exemplary Embodiments

Exemplary embodiments provided in accordance with the presently disclosed subject matter include, but are not limited to, the following:

1. A method for acquiring spectral data from a sample, the method comprising: injecting ions of the sample as a plurality of ion packets of the ions into an ion mobility (IM) drift cell over a drift time period according to a pseudorandom sequence (PRS) of ON pulses and OFF pulses, wherein each ON pulse injects one ion packet, and the drift time period is divided into a plurality of drift time blocks of equal duration, each drift time block comprising either a single ON pulse or no ON pulses; transmitting the ion packets through the IM drift cell, during which time two or more adjacent ion packets become overlapped in the IM drift cell; injecting the ions from the IM drift cell as a plurality of new ion packets into a time-of-flight (TOF) mass analyzer according to a sequence of TOF pulses; transmitting the new ion packets through the TOF mass analyzer to an ion detector; recording respective arrival times of the ions of each new ion packet at the ion detector to produce raw measurement data; and removing noise from the raw measurement data to produce modified raw measurement data.

2. The method of embodiment 1, wherein removing noise from the raw measurement data to produce modified measurement data comprises: arranging the raw measurement data into an array of data points, wherein the array comprises a plurality of columns corresponding to a total number of the drift time blocks, and a plurality of rows corresponding to a total number of TOF pulses performed during each drift time block; for each row, counting a total number of positive data points contained in the row, and determining whether the total number of positive data points is less than a threshold value, wherein: if the total number of positive data points is less than the threshold value, then setting all data points in the row to zero; and if the total number of positive data points is greater than or equal to the threshold value, then retaining all data points in the row.

3. The method of embodiment 1 or 2, comprising deconvoluting the PRS from the modified measurement data to produce deconvoluted measurement data.

4. The method of embodiment 3, comprising removing noise from the deconvoluted measurement data to produce modified deconvoluted measurement data.

5. The method of embodiment 3 or 4, comprising producing a drift time versus m/z ratio versus abundance spectrum from the deconvoluted measurement data or modified deconvoluted measurement data.

6. The method of any of embodiments 3 to 5, wherein deconvoluting comprises applying a transform algorithm to the modified measurement data.

7. The method of embodiment 6, wherein the transform algorithm is a Hadamard transform algorithm or a fast Hadamard transform algorithm.

8. A method for acquiring spectral data from a sample, the method comprising: injecting ions of the sample as a plurality of ion packets of the ions into an ion mobility (IM) drift cell over a drift time period according to a pseudorandom sequence (PRS) of ON pulses and OFF pulses, wherein each ON pulse injects one ion packet, and the drift time period is divided into a plurality of drift time blocks of equal duration, each drift time block comprising either a single ON pulse or no ON pulses; transmitting the new ion packets through the TOF mass analyzer to an ion detector; recording respective arrival times of the ions of each new ion packet at the ion detector to produce raw measurement data; deconvoluting the PRS from the raw measurement data to produce deconvoluted measurement data; and removing noise from the deconvoluted measurement data to produce modified deconvoluted measurement data.

9. The method of embodiment 4 or 8, wherein removing noise from the deconvoluted measurement data to produce modified deconvoluted measurement data comprises: arranging the deconvoluted measurement data into an array of data points, wherein the array comprises a plurality of columns corresponding to a total number of the drift time blocks, and a plurality of rows corresponding to a total number of TOF pulses performed during each drift time block; for each row, calculating a sum (S_total) of all data points in the row; finding all peaks in the row using a moving window; for each peak found, calculating a sum (Sum_p) of all data points in the window that includes the peak; sorting the found peaks in descending order by Sum_p; for the first peak in the descending order, deducting Sum_p for that peak from S_total to obtain a new value for S_total; for the next peak in in the descending order, deducting Sum_p for that peak from the new value for S_total to obtain another new value for S_total; repeating the deducting step for additional peaks in the descending order until the S_total value is close to zero, then stopping the deducting step; for each peak subjected to the deducting step, retaining all data points of the peak; and for each peak not subjected to the deducting step, setting all data points of the peak to zero.

10. The method of embodiment 8 or 9, comprising, before deconvoluting, removing noise from the raw measurement data to produce modified raw measurement data, wherein deconvoluting is performed on the modified raw measurement data.

11. A method for acquiring ion measurement data from a sample, the method comprising: acquiring raw measurement data from ions produced from the sample; and removing noise from the raw measurement data by: arranging the raw measurement data into an array of data points, the array comprising a plurality of columns and a plurality of rows; for each row, counting a total number of positive data points contained in the row, and determining whether the total number of positive data points is less than a threshold value, wherein: if the total number of positive data points is less than the threshold value, then setting all data points in the row to zero; and if the total number of positive data points is greater than or equal to the threshold value, then retaining all data points in the row.

12. The method of embodiment 1, wherein acquiring the raw measurement data comprises a step selected from the group consisting of: injecting ions into a spectrometer at a multiplexed injection rate; injecting ions into a spectrometer according to an ion injection sequence of ON pulses and OFF pulses, wherein each ON pulse injects an ion packet; injecting ions into a spectrometer according to a pseudorandom sequence of ON pulses and OFF pulses, wherein each ON pulse injects an ion packet; recording respective arrival times of ions at an ion detector; operating an ion mobility spectrometer; operating a time-of-flight mass spectrometer; operating an ion mobility-mass spectrometer; and a combination of two or more of the foregoing.

13. The method of embodiment 11 or 12, wherein the columns correspond to a total number of ON pulses and OFF pulses of an ion injection sequence, and the rows correspond to a total number of time-of-flight pulses performed during each ion injection sequence.

14. The method of embodiment 13, wherein the ON pulses and the OFF pulses correspond to respective drift time blocks.

15. The method of any of embodiments 11 to 13, wherein removing noise from the raw measurement data produces modified measurement data, and further comprising deconvoluting the modified measurement data.

16. The method of embodiment 15, wherein deconvoluting comprises deconvoluting an ion injection sequence from the modified measurement data.

17. The method of embodiment 16, wherein the ion injection sequence is a pseudorandom sequence.

18. The method of any of embodiments 15 to 17, wherein deconvoluting comprises applying a transform algorithm, a Hadamard transform algorithm, or a fast Hadamard transform algorithm to the modified measurement data.

19. The method of any of embodiments 15 to 18, wherein deconvoluting the modified measurement data produces deconvoluted measurement data, and further comprising producing a drift time spectrum from the deconvoluted measurement data, a mass spectrum from the deconvoluted measurement data, or both of the foregoing.

20. The method of any of embodiments 15 to 19, wherein deconvoluting the modified measurement data produces deconvoluted measurement data, and further comprising removing noise from the deconvoluted measurement data.

21. The method of embodiment 20, wherein removing noise from the deconvoluted measurement data comprises: arranging the deconvoluted measurement data into an array of data points, the array comprising a plurality of columns and a plurality of rows; for each row, calculating a row sum (S_total) of all data points in the row; finding all peaks in the row using a moving window; for each peak found, calculating a window sum (Sum_p) of all data points in the window that includes the peak; sorting the found peaks in descending order by the window sum Sum_p; for the first peak in the descending order, deducting the window sum Sum_p for that peak from the row sum S_total to obtain a new value for the row sum S_total; for the next peak in the descending order, deducting the window sum Sum_p for that peak from the new value for the row sum S_total to obtain another new value for the row sum S_total; repeating the deducting step for additional peaks in the descending order until the row sum S_total value is close to zero, then stopping the deducting step; for each peak subjected to the deducting step, retaining all data points of the peak; and for each peak not subjected to the deducting step, setting all data points of the peak to zero.

22. A method for acquiring ion measurement data from a sample, the method comprising: acquiring raw measurement data from ions produced from the sample; deconvoluting the raw measurement data to produce deconvoluted measurement data; and removing noise from the raw deconvoluted measurement data by: arranging the deconvoluted measurement data into an array of data points, the array comprising a plurality of columns and a plurality of rows; for each row, calculating a row sum (S_total) of all data points in the row; finding all peaks in the row using a moving window; for each peak found, calculating a window sum (Sum_p) of all data points in the window that includes the peak; sorting the found peaks in descending order by the window sum Sum_p; for the first peak in the descending order, deducting the window sum Sum_p for that peak from the row sum S_total to obtain a new value for the row sum S_total; for the next peak in the descending order, deducting the window sum Sum_p for that peak from the new value for the row sum S_total to obtain another new value for the row sum S_total; repeating the deducting step for additional peaks in the descending order until the row sum S_total value is close to zero, then stopping the deducting step; for each peak subjected to the deducting step, retaining all data points of the peak; and for each peak not subjected to the deducting step, setting all data points of the peak to zero.

23. The method of embodiment 22, wherein acquiring the raw measurement data comprises a step selected from the group consisting of: injecting ions into a spectrometer at a multiplexed injection rate; injecting ions into a spectrometer according to an ion injection sequence of ON pulses and OFF pulses, wherein each ON pulse injects an ion packet; injecting ions into a spectrometer according to a pseudorandom sequence of ON pulses and OFF pulses, wherein each ON pulse injects an ion packet; recording respective arrival times of ions at an ion detector; operating an ion mobility spectrometer; operating a time-of-flight mass spectrometer; operating an ion mobility-mass spectrometer; and a combination of two or more of the foregoing.

24. The method of embodiment 22 or 23, wherein deconvoluting comprises deconvoluting an ion injection sequence from the raw measurement data.

25. The method of embodiment 24, wherein the ion injection sequence is a pseudorandom sequence.

26. The method of any of embodiments 22 to 25, wherein deconvoluting comprises applying a transform algorithm, a Hadamard transform algorithm, or a fast Hadamard transform algorithm to the raw measurement data.

27. The method of any of embodiments 22 to 26, comprising producing a drift time spectrum from the deconvoluted measurement data, a mass spectrum from the deconvoluted measurement data, or both of the foregoing.

28. The method of any of embodiments 22 to 27, comprising, before deconvoluting, removing noise from the raw measurement data to produce modified raw measurement data, wherein deconvoluting is performed on the modified raw measurement data.

29. The method of embodiment 28, wherein removing noise from the raw measurement data comprises: arranging the raw measurement data into an array of data points, the array comprising a plurality of columns and a plurality of rows; for each row, counting a total number of positive data points contained in the row, and determining whether the total number of positive data points is less than a threshold value, wherein: if the total number of positive data points is less than the threshold value, then setting all data points in the row to zero; and if the total number of positive data points is greater than or equal to the threshold value, then retaining all data points in the row.

30. A method for acquiring ion measurement data from a sample, the method comprising: acquiring raw measurement data from ions produced from the sample; removing noise from the raw measurement data to produce modified measurement data; deconvoluting the modified measurement data to produce deconvoluted measurement data; and removing noise from the deconvoluted measurement data.

31. The method of embodiment 30, wherein removing noise from the raw measurement data comprises: arranging the raw measurement data into an array of data points, the array comprising a plurality of columns and a plurality of rows; for each row, counting a total number of positive data points contained in the row, and determining whether the total number of positive data points is less than a threshold value, wherein: if the total number of positive data points is less than the threshold value, then setting all data points in the row to zero; and if the total number of positive data points is greater than or equal to the threshold value, then retaining all data points in the row.

32. The method embodiment 30 or 31, wherein removing noise from the deconvoluted measurement data comprises: arranging the deconvoluted measurement data into an array of data points, the array comprising a plurality of columns and a plurality of rows; for each row, calculating a row sum (S_total) of all data points in the row; finding all peaks in the row using a moving window; for each peak found, calculating a window sum (Sum_p) of all data points in the window that includes the peak; sorting the found peaks in descending order by the window sum Sum_p; for the first peak in the descending order, deducting the window sum Sum_p for that peak from the row sum S_total to obtain a new value for the row sum S_total; for the next peak in the descending order, deducting the window sum Sum_p for that peak from the new value for the row sum S_total to obtain another new value for the row sum S_total; repeating the deducting step for additional peaks in the descending order until the row sum S_total value is close to zero, then stopping the deducting step; for each peak subjected to the deducting step, retaining all data points of the peak; and for each peak not subjected to the deducting step, setting all data points of the peak to zero.

33. A spectrometry system configured for receiving ion measurement data and performing all or part of the method of any of the preceding embodiments.

34. The spectrometry system of embodiment 33, comprising: an ion analyzer; an ion detector configured for receiving ions from the ion analyzer; and a computing device configured for receiving ion measurement data from the ion detector and performing all or part of the method of any of the preceding embodiments.

35. The spectrometry system of embodiment 34, wherein the computing device comprises a module selected from the group consisting of: a pseudorandom sequence generator, a deconvolution module, a pre-deconvolution module, a post-deconvolution module, and a combination of two or more of the foregoing.

36. The spectrometry system of embodiment 33 or 34, comprising an ion analyzer, and an ion gate configured for pulsing ions in ion packets toward the ion analyzer according to an ion injection sequence of ON pulses and OFF pulses, wherein each ON pulse injects an ion packet.

37. The spectrometry system of any of embodiments 34 to 36, wherein the ion analyzer comprises an ion mobility drift cell, an ion mobility drift cell followed by a mass analyzer, or a time-of-flight analyzer.

38. A system for acquiring ion measurement data from a sample, the system comprising: a processor and a memory configured for performing all or part of the method of any of the preceding embodiments.

39. The system of embodiment 38, comprising: a computing device; and an ion detector, wherein the computing device comprises the processor and the memory, and the ion detector is configured for transmitting ion measurement data to the computing device.

40. A computer-readable storage medium comprising instructions for performing all or part of the method of any of the preceding embodiments.

41. A system comprising the computer-readable storage medium of embodiment 40.

Methods for acquiring spectral data from a sample such as described above and illustrated in the Figures may be performed (carried out), for example, in a system that includes a processor and a memory as may be embodied in, for example, a computing device which may communicate with a user input device and/or a user output device. In some embodiments, the system for acquiring spectral data from a sample (or an associated computing device) may be considered as including the user input device and/or the user output device. A spectrometry system such as described above and illustrated in FIG. 1A may include, or be part of, or communicate with a system for acquiring spectral data from a sample. As used herein, the term "perform" or "carry out" may encompass actions such as controlling and/or signal or data transmission. For example, a computing device such as illustrated in FIGS. 1A and 1B, or a processor thereof, may perform a method step by controlling another component involved in performing the method step. Performing or controlling may involve making calculations, or sending and/or receiving signals (e.g., control signals, instructions, measurement signals, parameter values, data, etc.).

As used herein, an "interface" or "user interface" is generally a system by which users interact with a computing device. An interface may include an input (e.g., a user input device) for allowing users to manipulate a computing device, and may include an output (e.g., a user output device) for allowing the system to present information and/or data, indicate the effects of the user's manipulation, etc. An example of an interface on a computing device includes a graphical user interface (GUI) that allows users to interact with programs in more ways than typing. A GUI typically may offer display objects, and visual indicators, as opposed to (or in addition to) text-based interfaces, typed command labels or text navigation to represent information and actions available to a user. For example, an interface may be a display window or display object, which is selectable by a user of a computing device for interaction. The display object may be displayed on a display screen of a computing device and may be selected by and interacted with by a user using the interface. In one non-limiting example, the display of the computing device may be a touch screen, which may display the display icon. The user may depress the area of the touch screen at which the display icon is displayed for selecting the display icon. In another example, the user may use any other suitable interface of a computing device, such as a keypad, to select the display icon or display object. For example, the user may use a track ball or arrow keys for moving a cursor to highlight and select the display object.

It will be understood that one or more of the processes, sub-processes, and process steps described herein may be performed by hardware, firmware, software, or a combination of two or more of the foregoing, on one or more electronic or digitally-controlled devices. The software may reside in a software memory (not shown) in a suitable electronic processing component or system such as, for example, the computing device 118 schematically depicted in FIGS. 1A and 1B. The software memory may include an ordered listing of executable instructions for implementing logical functions (that is, "logic" that may be implemented in digital form such as digital circuitry or source code, or in analog form such as an analog source such as an analog electrical, sound, or video signal). The instructions may be executed within a processing module, which includes, for example, one or more microprocessors, general purpose processors, combinations of processors, digital signal processors (DSPs), or application specific integrated circuits (ASICs). Further, the schematic diagrams describe a logical division of functions having physical (hardware and/or software) implementations that are not limited by architecture or the physical layout of the functions. The examples of systems described herein may be implemented in a variety of configurations and operate as hardware/software components in a single hardware/software unit, or in separate hardware/software units.

The executable instructions may be implemented as a computer program product having instructions stored therein which, when executed by a processing module of an electronic system (e.g., the computing device 118 in FIGS. 1A and 1B), direct the electronic system to carry out the instructions. The computer program product may be selectively embodied in any non-transitory computer-readable storage medium for use by or in connection with an instruction execution system, apparatus, or device, such as an electronic computer-based system, processor-containing system, or other system that may selectively fetch the instructions from the instruction execution system, apparatus, or device and execute the instructions. In the context of this disclosure, a computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access memory (electronic); a read-only memory (electronic); an erasable programmable read only memory such as, for example, flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program may be electronically captured via, for instance, optical scanning of the paper or other medium, then compiled, interpreted, or otherwise processed in a suitable manner if necessary, and then stored in a computer memory or machine memory.

It will also be understood that the term "in signal communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A method for acquiring ion measurement data from a sample, the method comprising:
    acquiring raw measurement data generated by an ion detector; and
    removing noise from the raw measurement data by:
    arranging the raw measurement data into an array of data points, the array comprising a plurality of columns and a plurality of rows;
    for each row, counting a total number of positive data points contained in the row, and determining whether the total number of positive data points is less than a threshold value, wherein:
    if the total number of positive data points is less than the threshold value, then setting all data points in the row to zero; and
    if the total number of positive data points is greater than or equal to the threshold value, then retaining all data points in the row.

2. The method of claim 1, wherein acquiring the raw measurement data comprises a step selected from the group consisting of:
    injecting ions into a spectrometer at a multiplexed injection rate;
    injecting ions into a spectrometer according to an ion injection sequence of ON pulses and OFF pulses, wherein each ON pulse injects an ion packet;
    injecting ions into a spectrometer according to a pseudo-random sequence of ON pulses and OFF pulses, wherein each ON pulse injects an ion packet;
    recording respective arrival times of ions at an ion detector;
    operating an ion mobility spectrometer;
    operating a time-of-flight mass spectrometer;
    operating an ion mobility-mass spectrometer; and
    a combination of two or more of the foregoing.

3. The method of claim 1, wherein the columns correspond to a total number of ON pulses and OFF pulses of an ion injection sequence, and the rows correspond to a total number of time-of-flight pulses performed during each ion injection sequence.

4. The method of claim 3, wherein the ON pulses and the OFF pulses correspond to respective drift time blocks.

5. The method of claim 1, wherein removing noise from the raw measurement data produces modified measurement data, and further comprising deconvoluting the modified measurement data.

6. The method of claim 5, wherein deconvoluting comprises deconvoluting an ion injection sequence from the modified measurement data.

7. The method of claim 6, wherein the ion injection sequence is a pseudorandom sequence.

8. The method of claim 5, wherein deconvoluting comprises applying a transform algorithm, a Hadamard transform algorithm, or a fast Hadamard transform algorithm to the modified measurement data.

9. The method of claim 5, wherein deconvoluting the modified measurement data produces deconvoluted measurement data, and further comprising producing a drift time spectrum from the deconvoluted measurement data, a mass spectrum from the deconvoluted measurement data, or both of the foregoing.

10. The method of claim 5, wherein deconvoluting the modified measurement data produces deconvoluted measurement data, and further comprising removing noise from the deconvoluted measurement data.

11. A spectrometry system configured for receiving ion measurement data and performing the method of claim 1.

12. The spectrometry system of claim 11, comprising:
an ion analyzer;
an ion detector configured for receiving ions from the ion analyzer; and
a computing device configured for receiving ion measurement data from the ion detector and performing the method of claim 1.

13. The spectrometry system of claim 12, wherein the computing device comprises a module selected from the group consisting of: a pseudorandom sequence generator, a deconvolution module, a pre-deconvolution module, a post-deconvolution module, and a combination of two or more of the foregoing.

14. The spectrometry system of claim 11, comprising an ion analyzer, and an ion gate configured for pulsing ions in ion packets toward the ion analyzer according to an ion injection sequence of ON pulses and OFF pulses, wherein each ON pulse injects an ion packet.

15. The spectrometry system of claim 14, wherein the ion analyzer comprises an ion mobility drift cell, an ion mobility drift cell followed by a mass analyzer, or a time-of-flight analyzer.

16. A method for acquiring ion measurement data from a sample, the method comprising:
acquiring convoluted raw measurement data generated by an ion detector;
deconvoluting the raw measurement data to produce deconvoluted measurement data; and
removing noise from the raw deconvoluted measurement data by:
arranging the deconvoluted measurement data into an array of data points, the array comprising a plurality of columns and a plurality of rows;
for each row, calculating a row sum (S_total) of all data points in the row;
finding all peaks in the row using a moving window;
for each peak found, calculating a window sum (Sum_p) of all data points in the window that includes the peak;
sorting the found peaks in descending order by the window sum Sum_p;
for the first peak in the descending order, deducting the window sum Sum_p for that peak from the row sum S_total to obtain a new value for the row sum S_total;
for the next peak in the descending order, deducting the window sum Sum_p for that peak from the new value for the row sum S_total to obtain another new value for the row sum S_total;
repeating the deducting step for additional peaks in the descending order until the row sum S_total value is close to zero, then stopping the deducting step;
for each peak subjected to the deducting step, retaining all data points of the peak; and
for each peak not subjected to the deducting step, setting all data points of the peak to zero.

17. The method of claim 16, comprising, before deconvoluting, removing noise from the raw measurement data to produce modified raw measurement data, wherein deconvoluting is performed on the modified raw measurement data.

18. A method for acquiring ion measurement data from a sample, the method comprising:
acquiring convoluted raw measurement data generated by an ion detector;
removing noise from the raw measurement data to produce modified measurement data;
deconvoluting the modified measurement data to produce deconvoluted measurement data; and
removing noise from the deconvoluted measurement data.

19. The method of claim 18, wherein removing noise from the raw measurement data comprises:
arranging the raw measurement data into an array of data points, the array comprising a plurality of columns and a plurality of rows;
for each row, counting a total number of positive data points contained in the row, and determining whether the total number of positive data points is less than a threshold value, wherein:
if the total number of positive data points is less than the threshold value, then setting all data points in the row to zero; and
if the total number of positive data points is greater than or equal to the threshold value, then retaining all data points in the row.

20. The method claim 18, wherein removing noise from the deconvoluted measurement data comprises:
arranging the deconvoluted measurement data into an array of data points, the array comprising a plurality of columns and a plurality of rows;
for each row, calculating a row sum (S_total) of all data points in the row;
finding all peaks in the row using a moving window;
for each peak found, calculating a window sum (Sum_p) of all data points in the window that includes the peak;
sorting the found peaks in descending order by the window sum Sum_p;
for the first peak in the descending order, deducting the window sum Sum_p for that peak from the row sum S_total to obtain a new value for the row sum S_total;
for the next peak in the descending order, deducting the window sum Sum_p for that peak from the new value for the row sum S_total to obtain another new value for the row sum S_total;
repeating the deducting step for additional peaks in the descending order until the row sum S_total value is close to zero, then stopping the deducting step;
for each peak subjected to the deducting step, retaining all data points of the peak; and
for each peak not subjected to the deducting step, setting all data points of the peak to zero.

* * * * *

UNITED STATES PATENT AND TRADEMARK OFFICE
CERTIFICATE OF CORRECTION

PATENT NO. : 9,576,778 B2
APPLICATION NO. : 14/686569
DATED : February 21, 2017
INVENTOR(S) : Jun Wang Page 1 of 1

It is certified that error appears in the above-identified patent and that said Letters Patent is hereby corrected as shown below:

In the Specification

Column 17, Line 54, delete "$Sum_p = \Sigma_{i=s}^{s+w}(array[i])$" and insert -- $Sum_p = \sum_{i=s}^{s+w}(array[i])$ --, therefor.

Signed and Sealed this
Twentieth Day of February, 2018

Andrei Iancu
*Director of the United States Patent and Trademark Office*